United States Patent
Park

(10) Patent No.: US 11,600,382 B2
(45) Date of Patent: Mar. 7, 2023

(54) METHOD, ELECTRONIC DEVICE, AND STORAGE MEDIUM FOR PROVIDING RECOMMENDATION SERVICE

(71) Applicant: Samsung Electronics Co., Ltd., Gyeonggi-do (KR)

(72) Inventor: Kwansu Park, Gyeonggi-do (KR)

(73) Assignee: Samsung Electronics Co., Ltd

( * ) Notice: Subject to any disclaimer, the term of this patent is extended or adjusted under 35 U.S.C. 154(b) by 532 days.

(21) Appl. No.: 16/654,719

(22) Filed: Oct. 16, 2019

(65) Prior Publication Data

US 2020/0152310 A1    May 14, 2020

(30) Foreign Application Priority Data

Nov. 14, 2018  (KR) .......................... 10-2018-0140209

(51) Int. Cl.
*G16H 20/30* (2018.01)
*G16H 40/63* (2018.01)
(Continued)

(52) U.S. Cl.
CPC ........... *G16H 40/63* (2018.01); *A61B 5/0022* (2013.01); *A63B 24/0075* (2013.01);
(Continued)

(58) Field of Classification Search
CPC ........... A63B 24/0075; A63B 24/0087; A63B 2230/08; A63B 2230/04; G06V 40/10;
(Continued)

(56) References Cited

U.S. PATENT DOCUMENTS

2009/0111425 A1 * 4/2009 Forbes .................. G06Q 10/10
455/418
2009/0118100 A1   5/2009 Oliver et al.
(Continued)

FOREIGN PATENT DOCUMENTS

KR   20150068072   6/2015
KR   20160111079   9/2016
(Continued)

OTHER PUBLICATIONS

International Search Report dated Jan. 23, 2020 issued in counterpart application No. PCT/KR2019/013488, 9 pages.
(Continued)

*Primary Examiner* — Congvan Tran
(74) *Attorney, Agent, or Firm* — The Farrell Law Firm, P.C.

(57) ABSTRACT

An electronic device includes a housing, a communication module positioned inside the housing, a processor positioned inside the housing and operatively connected with the communication module, a sensor module operatively connected with the processor, and a memory positioned inside the housing and operatively connected with the communication module, the sensor module, and the processor. The memory stores instructions configured to, when executed, enable the processor to gather data related to a first user, send a request for a user group corresponding to a first category among a plurality of categories to an external server using the communication module, obtain the user group corresponding to the first category based on at least part of the data related to the first user from the external server using the communication module, and provide information about at least one second user in the obtained user group.

19 Claims, 21 Drawing Sheets

(51) Int. Cl.
*G16H 10/60* (2018.01)
*A61B 5/00* (2006.01)
*A63B 24/00* (2006.01)
*G06F 18/2323* (2023.01)
*G06V 10/74* (2022.01)
*G06V 10/762* (2022.01)
*G06V 40/10* (2022.01)
*G06V 40/20* (2022.01)

(52) U.S. Cl.
CPC ...... *A63B 24/0087* (2013.01); *G06F 18/2323* (2023.01); *G06V 10/761* (2022.01); *G06V 10/763* (2022.01); *G06V 40/10* (2022.01); *G06V 40/23* (2022.01); *G16H 10/60* (2018.01); *G16H 20/30* (2018.01); *A63B 2230/04* (2013.01); *A63B 2230/08* (2013.01)

(58) Field of Classification Search
CPC .... G06V 40/23; G06K 9/6223; G06K 9/6224; G06K 9/6215; G16H 20/70; G16H 40/67; G16H 40/63; G16H 10/60; G16H 20/30; A61B 5/0022; G06Q 10/10
See application file for complete search history.

(56) References Cited

U.S. PATENT DOCUMENTS

| | | |
|---|---|---|
| 2013/0203475 A1 | 8/2013 | Kil et al. |
| 2014/0122494 A1 | 5/2014 | Thurston et al. |
| 2015/0066174 A1 | 3/2015 | Dugan |
| 2015/0296044 A1 | 10/2015 | Liu |
| 2016/0042651 A1* | 2/2016 | Joao ........................ G09B 19/00 434/309 |
| 2016/0171582 A1* | 6/2016 | Linden ...................... B60J 1/02 705/26.62 |
| 2017/0330297 A1* | 11/2017 | Cronin .................. A61B 5/6802 |
| 2018/0056130 A1 | 3/2018 | Bitran et al. |
| 2018/0089770 A1* | 3/2018 | Bostick .................. G06Q 50/12 |
| 2018/0178064 A1 | 6/2018 | Nah et al. |
| 2018/0227706 A1 | 8/2018 | Cho et al. |
| 2018/0285463 A1* | 10/2018 | Choi .................... G06F 16/9535 |
| 2018/0374386 A1* | 12/2018 | Benefield ........... A63B 24/0059 |
| 2019/0108536 A1* | 4/2019 | Benamara ............. G06Q 50/01 |
| 2020/0054266 A1* | 2/2020 | Hirobe ................... G16H 20/60 |

FOREIGN PATENT DOCUMENTS

| | | |
|---|---|---|
| KR | 10-1689555 | 12/2016 |
| KR | 1020160149100 | 12/2016 |

OTHER PUBLICATIONS

European Search Report dated Mar. 12, 2020 issued in counterpart application No. 19204883.3-1126, 8 pages.

Korean Office Action dated Dec. 12, 2022 issued in counterpart application No. 10-2018-0140209, 13 pages.

* cited by examiner

| Sector Id | Sector (total factors) | Frequency | Factor |
|---|---|---|---|
| SID-1 | USER INFORMATION (5) | WHEN INPUT BY USER<br>WHEN MEASURED | AGE<br>GENDER<br>HEIGHT<br>WEIGHT<br>COUNTRY |
| SID-2 | COMPETITION INFORMATION (3) | WHEN COMPETITION ENDS | WINNING RATE<br>TIE (END NORMALLY)<br>TIE (ABANDON COMPETITION) |
| SID-3 | ACTIVITY INFORMATION (32*11) | DAILY AVERAGE<br>DAILY MAXIMUM<br>AVERAGE PER WEEKDAY<br>MAXIMUM PER WEEKDAY<br>AVERAGE PER PERIOD OF TIME<br>MAXIMUM PER PERIOD OF TIME | MOVING TIME<br>MOVING DISTANCE<br>CALORIE CONSUMPTION<br>MOVING DISTANCE ON ASCENT<br>MOVING DISTANCE ON DESCENT<br>ALTITUDE<br>EXERCISE STRENGTH<br>HEARTRATE<br>BLOOD SUGAR<br>BLOOD PRESSURE<br>KIND OF EXERCISE |
| SID-4 | ENVIRONMENT INFORMATION (20) | DAILY AVERAGE<br>AVERAGE OF LAST SEVEN DAYS<br>AVERAGE OF LAST 30 DAYS<br>AVERAGE OF LAST 180 DAYS<br>AVERAGE OF LAST 360 DAYS | TEMPERATURE<br>HUMIDITY<br>AIR PRESSURE<br>RAINFALL |
| SID-5 | DIET INFORMATION (32*3) | DAILY AVERAGE<br>DAILY MAXIMUM<br>AVERAGE PER WEEKDAY<br>MAXIMUM PER WEEKDAY<br>AVERAGE PER PERIOD OF TIME<br>MAXIMUM PER PERIOD OF TIME | CALORIE OF INTAKE<br>WATER<br>CAFFEINE |
| SID-6 | SLEEP INFORMATION (32*2) | DAILY AVERAGE<br>DAILY MAXIMUM<br>AVERAGE PER WEEKDAY<br>MAXIMUM PER WEEKDAY<br>MAXIMUM PER PERIOD OF TIME | SLEEP TIME<br>SLEEP QUALITY |
| SID-7 | SERVICE USE (32*1) | DAILY AVERAGE<br>DAILY MAXIMUM<br>AVERAGE PER WEEKDAY<br>MAXIMUM PER WEEKDAY<br>AVERAGE PER PERIOD OF TIME<br>MAXIMUM PER PERIOD OF TIME | USE TIME OF APPLICATION |
| SID-8 | 3rd PARTY DEVICE USE (32*2) | DAILY AVERAGE<br>DAILY MAXIMUM<br>AVERAGE PER WEEKDAY<br>MAXIMUM PER WEEKDAY<br>AVERAGE PER PERIOD OF TIME<br>MAXIMUM PER PERIOD OF TIME | USE TIME OF WATCH<br>USE TIME OF CADENCE |

FIG.6

METHOD, ELECTRONIC DEVICE, AND STORAGE MEDIUM FOR PROVIDING RECOMMENDATION SERVICE

CROSS-REFERENCE TO RELATED APPLICATION(S)

This application is based on and claims priority under 35 U.S.C. § 119 to Korean Patent Application No. 10-2018-0140209, filed on Nov. 14, 2018, in the Korean Intellectual Property Office, the disclosure of which is incorporated by reference herein in its entirety.

BACKGROUND

1. Field

The present disclosure generally relates to methods, electronic devices, and storage media for providing a recommendation service.

2. Description of Related Art

More and more services and functions are being provided through electronic devices, e.g., smartphones, or other portable electronic devices. In particular, wearable smartwatches, smart glasses, or other wearable devices have begun to be used together with other portable electronic device, e.g., smartphone or tablet PC.

Such electronic devices may provide various healthcare functions using their embedded sensors. For example, an electronic device may measure the user's distance or count steps based on sensor information to provide an amount of exercise, or may measure and provide heartrate information using a heartrate sensor. A plurality of electronic devices may interwork with each other to provide a healthcare service. For example, based on exercise information or health information gathered by a wearable device, an electronic device may provide health-related information to the user, thus allowing the user to check on his or her overall health condition.

There are various health-care services which measure and record the user's activity or exercise information for promoting a healthy life, such as those which are offered by an S-health application. These services, which may be provided by smartphones, encourage users to have good health by competition and encouragement using social relationships.

Thus, it may be beneficial to provide electronic devices which are capable of providing services to promote and improve user's health using social relationships.

SUMMARY

The present disclosure has been made to address the above-mentioned problems and disadvantages, and to provide at least the advantages described below.

In accordance with an aspect of the present disclosure, an electronic device is provided and includes a housing, a communication module positioned inside the housing, a processor positioned inside the housing and operatively connected with the communication module, a sensor module operatively connected with the processor, and a memory positioned inside the housing and operatively connected with the communication module, the sensor module, and the processor. The memory stores instructions configured to, when executed, enable the processor to gather data related to a first user, send a request for a user group corresponding to a first category among a plurality of categories to an external server using the communication module, obtain the user group corresponding to the first category based on at least part of the data related to the first user from the external server using the communication module, and provide information about at least one second user in the obtained user group.

In accordance with another aspect of the present disclosure, an electronic device is provided and includes a communication module, a processor, and a memory operatively connected with the communication module and the processor. The memory stores instructions configured to, when executed, enable the processor to receive data related to a first user of an external electronic device from the external electronic device using the communication module, receive a request for a user group corresponding to a first category among a plurality of categories from the external electronic device using the communication module, obtain the user group corresponding to the first category based on at least part of the first user-related data, in response to the reception of the request, and provide information about at least one second user in the obtained user group to the external electronic device using the communication module.

In accordance with another aspect of the present disclosure, a method for providing a recommendation service on an electronic device includes gathering data related to a first user, sending a request for a user group corresponding to a first category among a plurality of categories to a server, obtaining the user group corresponding to the first category based on at least part of the first user-related data, and providing information about at least one second user in the obtained user group.

In accordance with another aspect of the present disclosure a non-transitory storage medium storing instructions is provided, the instructions are configured to be executed by at least one processor to enable the at least one processor to perform at least one operation. The at least one operation includes gathering data related to a first user, sending a request for a user group corresponding to a first category among a plurality of categories to an external server, obtaining the user group corresponding to the first category based on at least part of the first user-related data, and providing information about at least one second user in the obtained user group.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 6 is a view illustrating an example table of classifying user-related data according to a plurality of data types, according to an embodiment;

DETAILED DESCRIPTION

Figure 1:
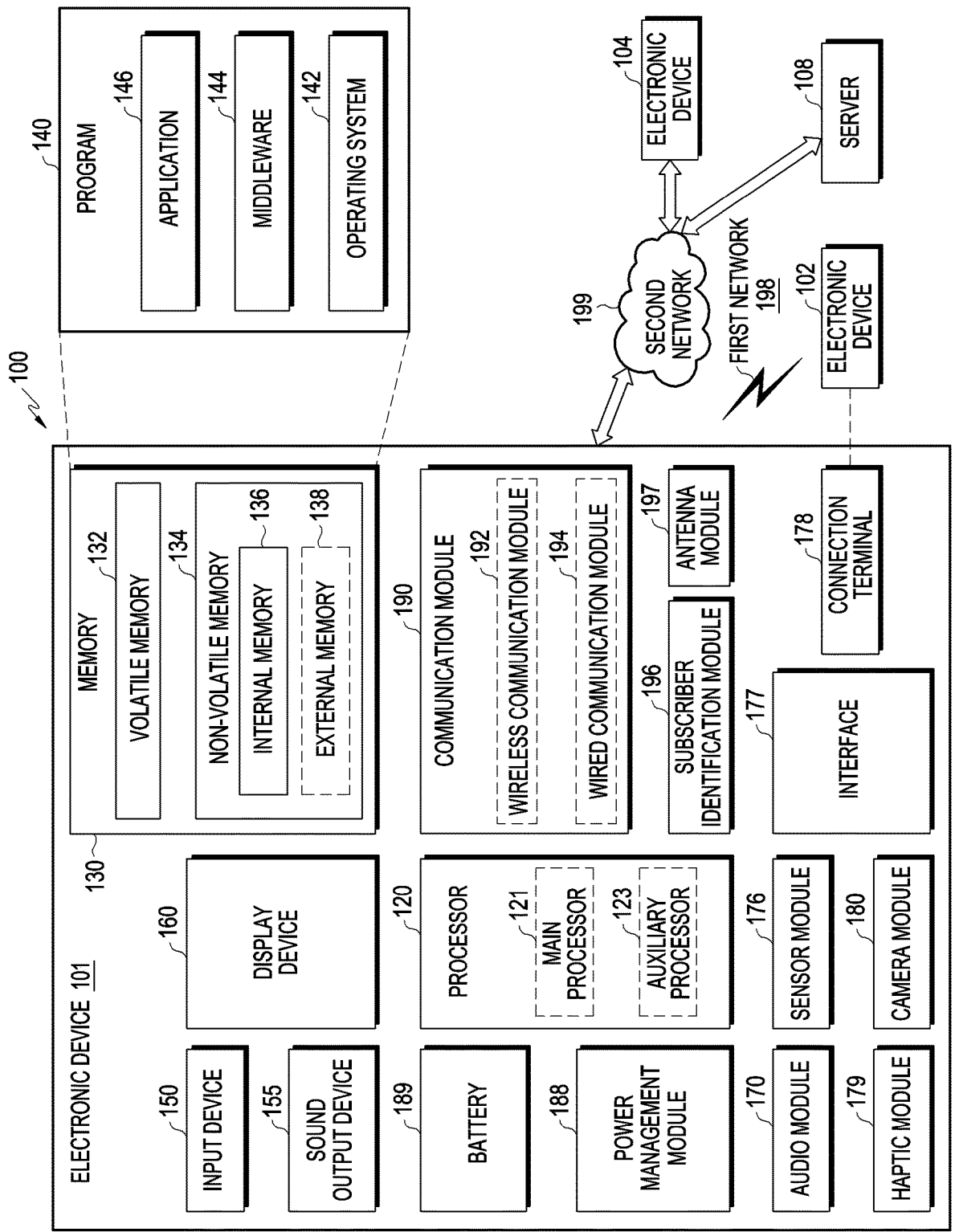
FIG. 1 is a view illustrating an electronic device in a network environment, according to an embodiment.

Various embodiments of the present disclosure are described with reference to the accompanying drawings. However, various embodiments of the present disclosure are not limited to particular embodiments, and it should be understood that modifications, equivalents, and/or alternatives of the embodiments described herein can be variously made. With regard to description of drawings, similar components may be marked by similar reference numerals.

The terms as used herein are provided merely to describe some embodiments thereof, but not to limit the scope of other embodiments of the disclosure. It is to be understood that the singular forms "a," "an," and "the" include plural references unless the context clearly dictates otherwise. All terms including technical and scientific terms used herein have the same meaning as commonly understood by one of ordinary skill in the art to which the embodiments of the disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some cases, the terms defined herein may be interpreted to exclude embodiments of the disclosure.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in nonvolatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by another component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing a record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between like electronic device 101 and the external electronic device (e.g., the electronic device 102, the electronic device 104, or the server 108) and performing communication via the established communication channel. The communication module 190 may include one or more communication processors that are operable independently from the processor 120 (e.g., the AP) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or Infrared Data Association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of the operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
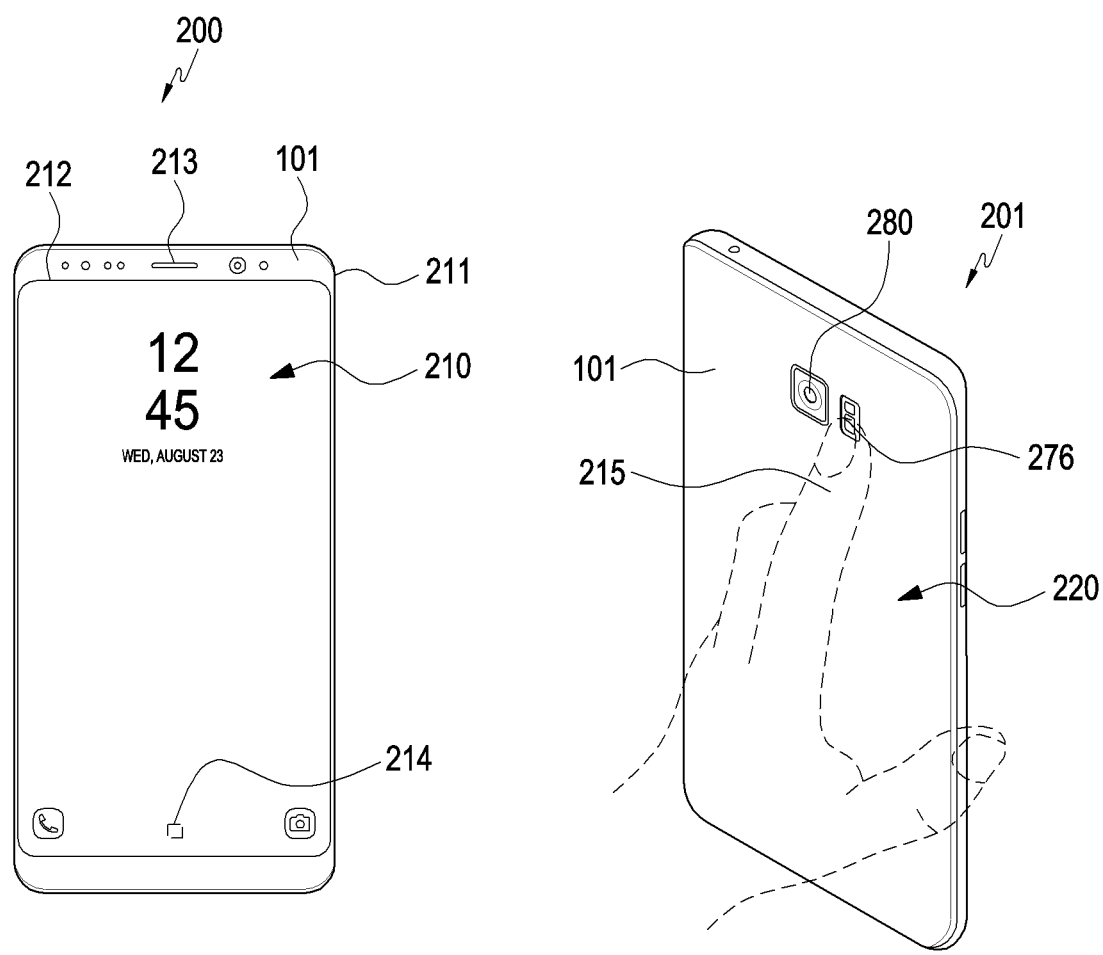
FIG. 2 is an example view illustrating the outer appearance of an electronic device, according to an embodiment.

FIG. 2 illustrates example views 200 and 201 illustrating the outer appearance of an electronic device, according to an embodiment.

FIG. 2 illustrates the front appearance 200 and rear appearance 201 of the electronic device 101. Referring to FIG. 2, the electronic device 101 includes a housing 211, a display 212, and a speaker 213.

The housing 211 may provide a space for receiving components (e.g., the display 212 or the speaker 213). The housing 211 may be implemented in various forms.

The display 212 may be positioned on the front surface 210 of the housing 211. The display 212 may be in the form of a touchscreen overlaid on a touch panel. The display 212 may include a curved surface. For example, the display 212 may have curved surfaces at the edges thereof.

The speaker 213 may be positioned at the top of the display 212 disposed on the front surface 210 to output voice signals. A home key 214 which is of a soft key type may be positioned at the bottom of the display 212.

The electronic device 101 may be equipped with components for performing various functions. The components may include at least one sensor module. The sensor module may have the same or similar configuration to the sensor module 176 of FIG. 1. For example, at least one of an illuminance sensor (e.g., a light sensor), a proximity sensor, an IR sensor, or an ultrasonic sensor may be disposed around the speaker 213. The sensor module may include a motion sensor, such as a gyro sensor or geomagnetic sensor, as opposed to an acceleration sensor, and may obtain information about the user's motion in relation to the activity of the user of the electronic device 101. The sensor module may include at least one biometric sensor (e.g., a heartrate sensor) which is capable of measuring the user's biometric information.

A biometric sensor 276 may be disposed on the rear surface 220 (e.g., the surface positioned away from the surface where the display 212 is disposed). For example, the biometric sensor 276 may be disposed adjacent the camera module 280. A fingerprint sensor may be disposed on the rear surface 220 of the electronic device 101, separately from the biometric sensor 276. The fingerprint sensor may be placed on a side surface of the electronic device 101 or positioned inside the display 212 disposed on the front surface 210. For example, when the fingerprint sensor is disposed on the side surface of the electronic device 101, it may be easy for the user to touch the fingerprint sensor with his or her thumb while grabbing the electronic device 101 as shown in the rear appearance 201 of the electronic device 101. Since the user is able to obtain fingerprint information with the electronic device 101 in his or her hand, if there is a plurality of users who use the electronic device 101, the plurality of users may be distinguished from each other based on input fingerprint information. The electronic device 101 may manage data related to each user based on biometric information about the plurality of users or signals for identifying the biometric information.

The biometric information or signals for identifying the biometric information may be obtained as the user's body portion (e.g., the user's finger) 215 touches or approaches the biometric sensor 276. The biometric information or signals for identifying the biometric information may be obtained in various manners depending on the position where the biometric sensor 276 is placed in the electronic device 101.

The electronic device 101 may obtain at least one piece of sensor data, which is produced as the user moves, using at least one sensor included in the sensor module. The electronic device 101 may determine the user's activity (e.g., workout or sleep) based on the at least one piece of sensor data obtained. For example, the electronic device 101 may identify the user's activity state, e.g., squatting, jogging, swimming, biking, walking, or hiking, based on the at least one piece of sensor data obtained by the sensor module. The electronic device 101 may interwork (i.e., connect) with a wearable electronic device, e.g., a wearable device or health band, to be able to obtain data related to the user's activity. For example, when interworking (i.e., connecting) with a wearable device, the electronic device 101 may obtain the user activity-related data from the wearable device. A watch-type wearable device, as an example of the wearable device, is described below with reference to FIGS. 3A and 3B.

Figure 3A:
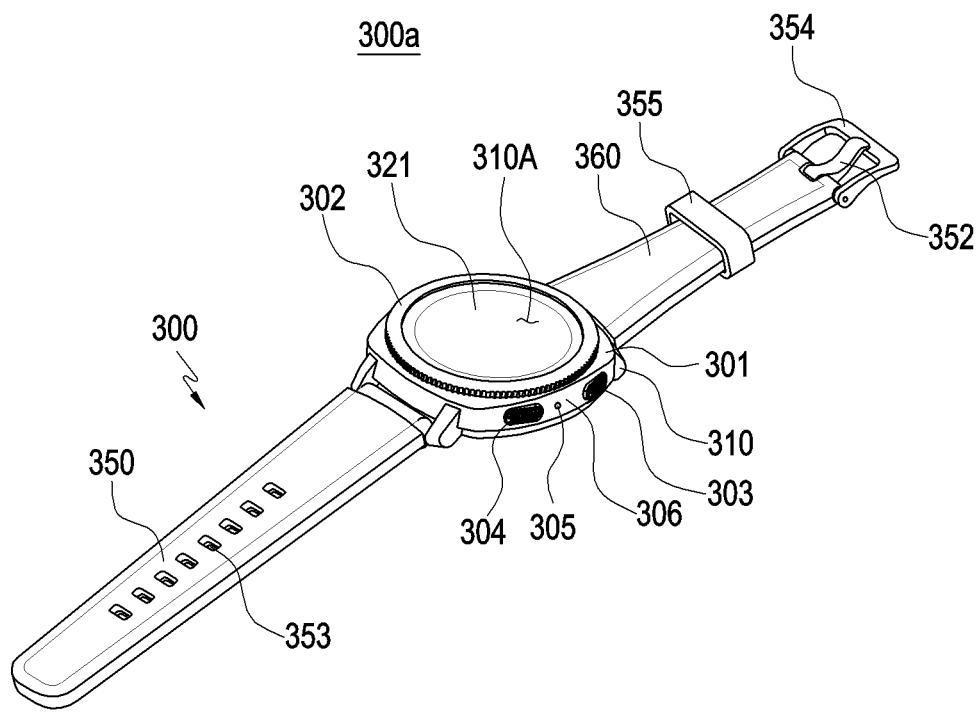
FIG. 3A is a front perspective view illustrating a wearable device, according to an embodiment.

FIG. 3A is a perspective view 300*a* illustrating the front surface of a wearable device, according to an embodiment.

Figure 3B:
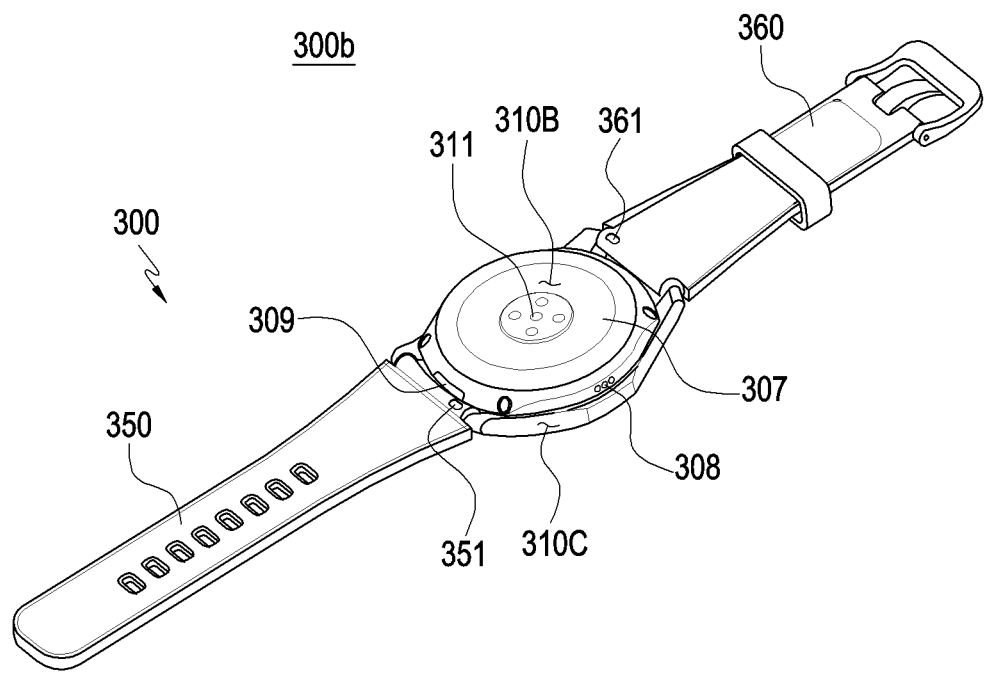
FIG. 3B is a rear perspective view illustrating the wearable device of FIG. 3A, according to an embodiment.

FIG. 3B is a perspective view 300*b* illustrating the rear surface of the wearable device of FIG. 3A, according to an embodiment.

Referring to FIGS. 3A and 3B, the wearable device 300 includes a housing 310 including a first surface (or front surface) 310A, a second surface (or rear surface) 310B, a side surface 310C surrounding the space between the first surface 310A and the second surface 310B, and coupling members 350 and 360 connected to at least part of the housing 310 and configured to allow the wearable device 300 to be removably worn on a portion of the user's body (e.g., the user's wrist or ankle).

The housing may denote a structure forming part of the first surface 310A, the second surface 310B, and the side surface 310C of FIG. 3A. At least part of the first surface 310A may have a substantially transparent front plate 301 (e.g., a glass plate or polymer plate including various coat layers). The second surface 310E may be formed of a substantially opaque rear plate 307. The rear plate 307 may be formed of laminated or colored glass, ceramic, polymer, metal (e.g., aluminum, stainless steel (STS), or magnesium), or a combination of at least two thereof.

The side surface 310C may be formed by a side bezel structure (or a "side member") 306 that couples to the front plate 301 and the rear plate 307 and includes a metal and/or polymer. The rear plate 307 and the side bezel plate 306 may be integrally formed together and include the same material (e.g., a metal, such as aluminum). The coupling members 350 and 360 may be formed of various materials in various shapes. A uni-body structure or multiple unit links which are flexible may be formed of fabric, leather, rubber, urethane, metal, ceramic, or a combination of at least two thereof.

The wearable device 300 may include at least one or more of a display 321, audio modules 305 and 308, a sensor module 311, key input devices 303 and 304, and a connector hole 309. The electronic device 300 may exclude at least one (e.g., the key input devices 303 and 304, connector hole 309, or sensor module 311) of the components or may add other components.

The display 321 may be exposed through a considerable portion of the front plate 301. The display 321 may have a shape corresponding to the shape of the front plate 301, e.g., a circle, ellipse, or polygon. The display 321 may be coupled with, or disposed adjacent to, a touch detection circuit, a pressure sensor capable of measuring the strength (pressure) of touches, and/or a fingerprint sensor.

The audio modules 305 and 308 may include a microphone hole 305 and a speaker hole 308. The microphone hole 305 may have a microphone inside to obtain external sounds. There may be a plurality of microphones to be able to detect the direction of a sound. The speaker hole 308 may be used for an external speaker or a receiver for phone talks. The speaker hole 308 and the microphone hole 305 may be implemented as a single hole, or a speaker may be included without the speaker hole 308 (e.g., a piezo speaker).

The sensor module 311 may produce an electrical signal or data value corresponding to the internal operation state or external environment state of the wearable device 300. The sensor module 311 may include a biometric sensor module 311 (e.g., a heartrate monitor (HRM) sensor) disposed on the second surface 310B of the housing 310. The wearable device 300 may further include sensor modules not shown, e.g., at least one of a gesture sensor, a gyro sensor, an atmospheric pressure sensor, a magnetic sensor, an acceleration sensor, a grip sensor, a color sensor, an IR sensor, a biometric sensor, a temperature sensor, a humidity sensor, or an illuminance sensor.

A wheel key 302 may be a key input device disposed on the first surface 310A of the housing 310 to be rotatable in at least one direction. Key buttons 303 and 304 may be disposed on the side surface 310C of the housing 310. The wheel key 302 may have a shape corresponding to the shape of the front plate 301. The wearable device 300 may exclude all or some of the above-mentioned wheel key 302 and key input devices 303 and 304. The excluded wheel key 302 and key input devices 303 and 304 may be implemented in other forms, e.g., as soft keys on the display 321.

The connector hole 309 may receive a connector (e.g., a USB connector) for transmitting and receiving power and/or data to/from an external electronic device. Another connector hole may be included for receiving a connector for transmitting and receiving audio signals to/from the external electronic device. The wearable device 300 may further include a connector cover to cover at least part of the connector hole 309 and to prevent undesirable materials from entering the connector hole.

The coupling members 350 and 360 may detachably be fastened to at least some portions of the housing 310 via locking members 351 and 361. The coupling members 350 and 360 may include one or more of a fastening member 352, fastening member coupling holes 353, a band guide member 354, and a band fastening ring.

The fastening member 352 may be configured to allow the housing 310 and the coupling members 350 and 360 to be fastened to the portion of the user's body (e.g., wrist or ankle). The fastening member coupling holes 353 may fasten the housing 310 and the coupling members 350 and 360 to the portion of the user's body, corresponding to the fastening member 352. The band guide member 354 may be configured to restrict movement of the fastening member 352 to a certain range when the fastening member 352 fits into one of the fastening member coupling holes 353, thereby allowing the coupling members 350 and 360 to be tightly fastened onto the portion of the user's body. The band fastening ring 355 may limit the range of movement of the coupling members 350 and 360, with the fastening member 352 fitted into one of the fastening memory coupling holes 353.

The wearable device 300 may be worn on the user's body and may obtain sensor data using the sensor module 311 included in the wearable device 300. The wearable device 300 may detect the user's biometric information (or biometric signal) using a biometric sensor included in the sensor module 311. The wearable device 300 may gather data related to the user's activity using biometric information and sensor data obtained from the sensor module 311 including at least one of a gyro sensor, a gravity sensor, a geo-magnetic sensor, or an acceleration sensor.

Figure 4A:
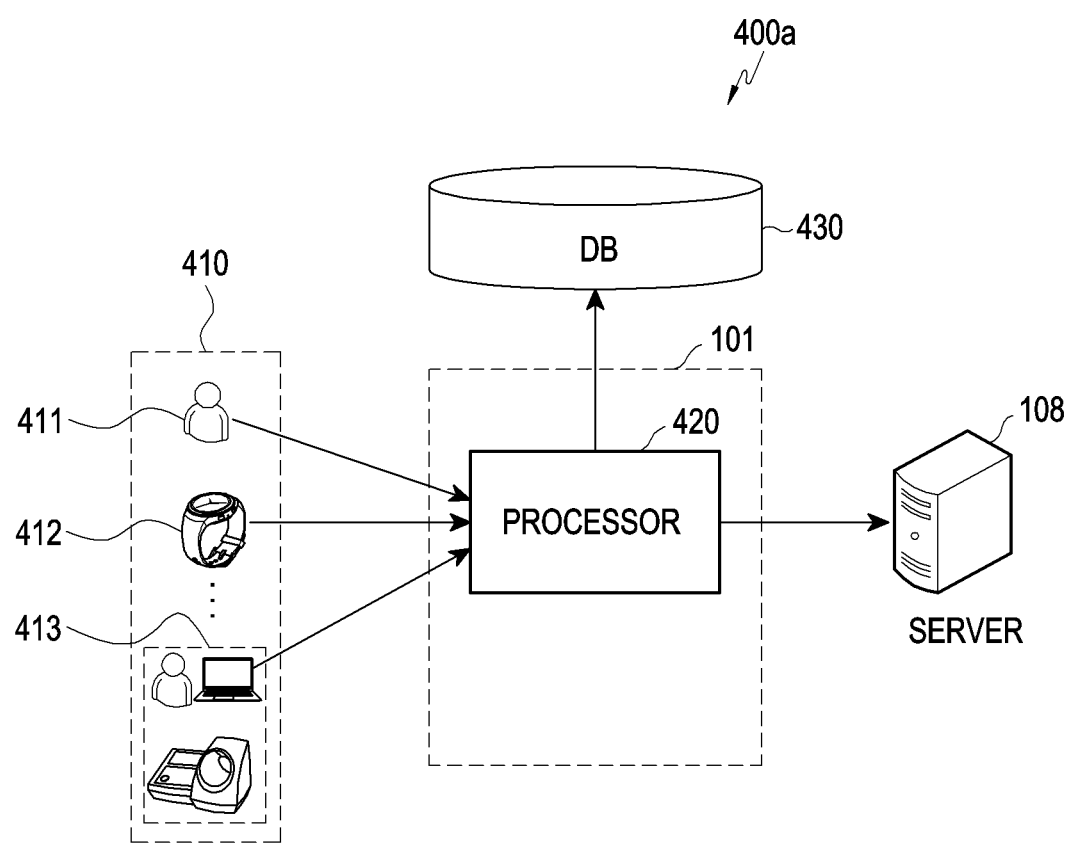
FIG. 4A is a concept view illustrating a recommendation service, according to an embodiment.

FIG. 4A is a concept view 400*a* illustrating a recommendation service, according to an embodiment.

Referring to FIG. 4A, the processor 420 of the electronic device 101 obtains data related to the user of the electronic device 101. At least one piece of sensor data may be obtained which is produced according to the user's activity using the sensor module 176 or the biometric sensor 276. The processor 420 may receive at least one piece of user-related data, such as diet information, sleep information, or personal information directly from the user 411. The processor 420 may receive user-related data from the wearable device 412 while the user is wearing the wearable device 412 and the electronic device 101 is connected with the wearable device 412. For example, the processor 420 may gather the user-related data by obtaining at least one of user information and information about the ambient environment around the wearable device 412 using the sensor module 311. The wearable device 412 may provide the user-related data gathered by the wearable device 412 directly to the server 108 through a communication module which enables wireless communication between the wearable device 412 and the server 108.

The processor 420 may receive the user-related data measured by a third party device 413. The third party device 413 may be any type which is capable of sensing or measuring at least one of the user information and the information about the environment around the user using the third party device 413. The third party device 413 may be one of various portable medical measuring devices and may be a device which is attached onto a piece of exercise equipment to measure the user activity-related data. For example, when the user rides a bicycle or uses a treadmill, the user's activity, such as biking, walking, running, or hiking may be identified based on sensor data obtained by the third party device 413 which is attached onto the bicycle or treadmill, and user-related data corresponding to the identified user activity may be received. The third party device 413 may provide the user-related data including the user's ambient environment information. For example, the third party device 413 may provide the user's ambient environment information including at least one of weather, temperature, humidity, air pressure, or rainfall.

The processor 420 may gather user-related data and store the gathered user-related data in a memory 130. The processor 420 may store the gathered user-related data in the memory, thereby producing a database 430. The processor 420 may gather the user-related data and update the database 430, thereby keeping the database 430 up to date.

The user-related data gathered as set forth above may be big data having a high-volume, multi-dimensional feature. Thus, the processor 420 may classify the user-related sensor data per data type and quantify the data corresponding to each data type. The processor 420 may store the user-related data quantified per data type in the database 430 and transmit it to the server 108. For example, the processor 420 may transmit the quantified user-related data to the server 108 at predetermined periods or periods determined by the server 108. The period and frequency of transmission may be preset, but is not limited thereto.

The processor 420 of the electronic device 101 is able to process high-volume data and may thus quantify the user-related data per data type. However, the data processing capacity of the wearable device 412 may be limited. Thus, the server 108 may classify the user-related data gathered from the wearable device 412 per data type, quantify the data corresponding to each data type, and then store it. Similarly, if the third party device 413 has a communication module by which it may communicate with the server 108, it may directly provide the gathered user-related data to the server 108, and to the wearable device 412.

Figure 4B:
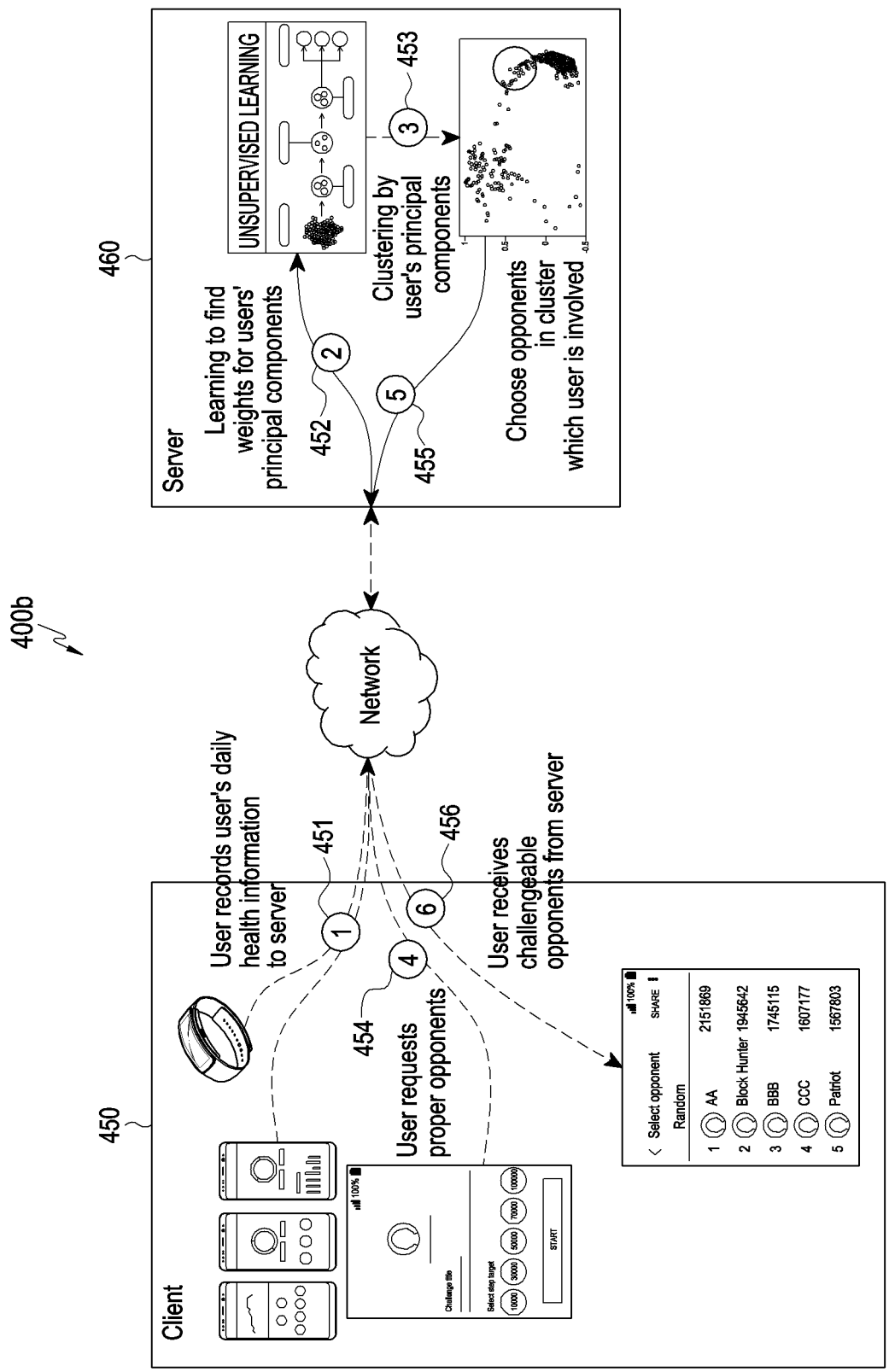
FIG. 4B is an example view illustrating an order of operation based on the components of FIG. 4A, according to an embodiment.

FIG. 4B is an example view 400b illustrating an order of operation based on the components of FIG. 4A.

Referring to FIG. 4B, the device gathering user-related data may be referred to as a client 450. For example, the client 450 may include at least one of an electronic device 101 a wearable device, or a third party device 413. The client 450 may receive user-related data from at least one of an electronic device, a wearable device, or a third party device. For example, in a first step 451, the client 450 may record the user's routine health information in the server 460. In a second step 452, the server 460 may obtain the user-related data and apply a feature extraction model for reducing the dimension of the user-related data, thereby clustering it in a third step 453. Next, when the client 450 sends a request in a fourth step 454 for a competitor to the server 460, the server 460 may select at least one competitor from the cluster where the user belongs in a fifth step 455. Thus, the client 450 may receive a challengeable competitor from the server 460 in a sixth step 456. The client 450 may provide a user interface for user input, such as for a selection of a category or a request for a competitor. The client 450 may recommend the most similar competitor to the user according to the user's request through the user interface and may provide the user's health condition trend and competitor information. To be meaningful or effective in all kinds of exercise, competition needs to be made in the same environment and among those with similar physical conditions and skills.

It is possible to recommend a user-customized competitor by learning such user-related data as user personal information, activity information, exercise record information, diet information, sleep information, or environment information in the recommendation service for healthcare. For example, in competitor matching, a competitor may be recommended by clustering other users who have similar physical conditions or exercise propensity and similar exercise goals (e.g., losing 5 kilograms (kg) of body fat) to the user. As such, rather than recommending friends or any user as competitors by comparison of simplified information, e.g., activity comparison, competitors may be recommended by clustering those who are most similar in activity pattern to the user based on all data that overall influences the user's healthcare as well as the user's propensities. This may encourage the user's desire for maintaining good healthcare and to keep using the healthcare service.

Figure 5:
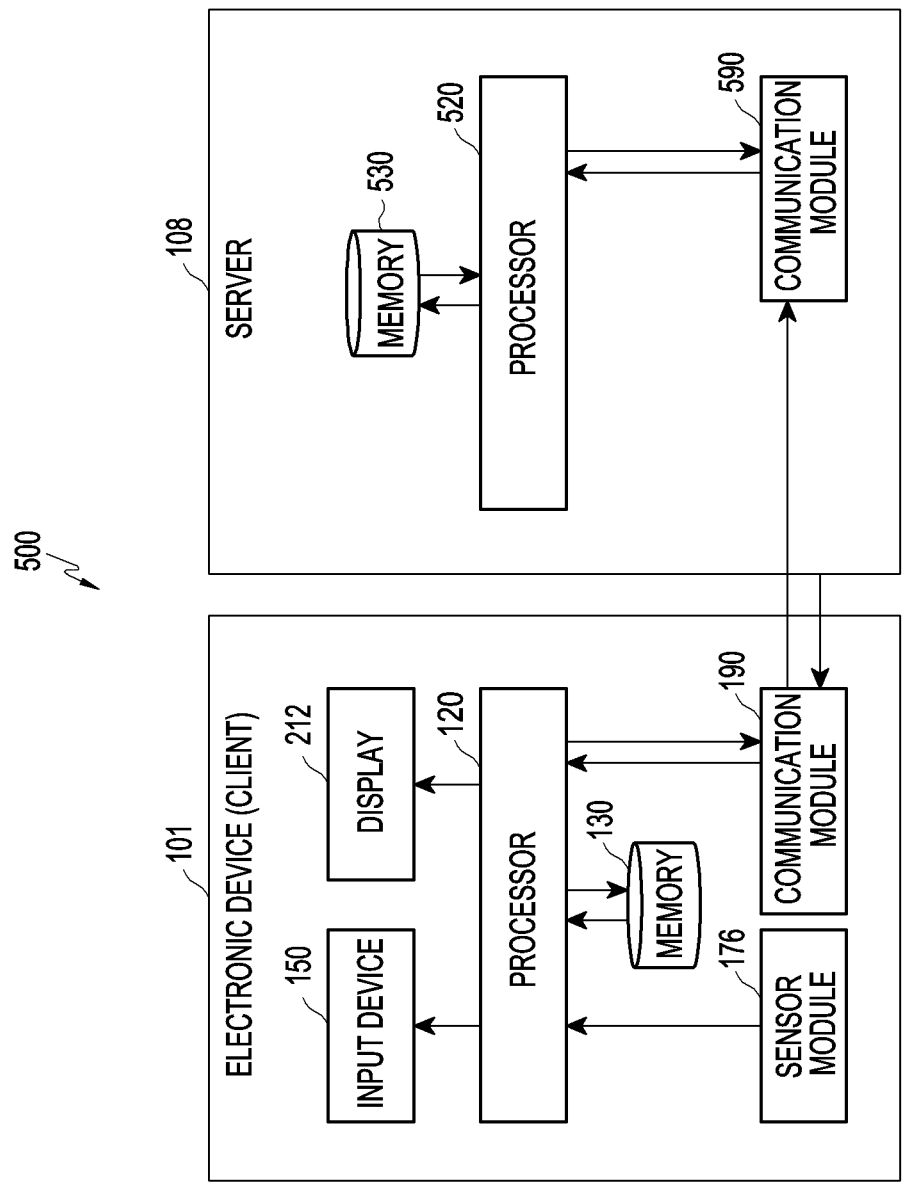
FIG. 5 is a block diagram illustrating the inner configurations of an electronic device and a server, according to an embodiment.

FIG. 5 is a block diagram 500 illustrating internal configurations of an electronic device and a server, according to an embodiment.

Referring to FIG. 5, the electronic device 101 may be a device which provides a user-related data-based recommendation service. The electronic device 101 may include a housing, a communication module 190 positioned inside the housing to perform communication with an external server, a processor 120 positioned inside the housing and operatively connected with the communication module 190, a sensor module 176 operatively connected with the processor 120, and a memory 130 positioned inside the housing and operatively connected with the communication module 190, the sensor module 176, and the processor 120. The electronic device 101 may include an input device 150 and a display 212. Not all of the components of FIG. 5 are essential ones of the electronic device 101 but the electronic device 101 may be implemented with more or less components than illustrated in FIG. 5.

The input device 150 may be provided for receiving information from the user. When user information is input through the input device 150, the processor 120 may control the operation of the electronic device 101 corresponding to the input user information. For example, the user may input various types of data related to the user's activity, such as diet information, sleep information, or personal information, through the input device 150, and such user-related data may be gathered periodically or a periodically.

The display 212 may output a user interface for providing a user-related recommendation service. For example, the display 212 may output a list of other parties similar in propensity to the user based on at least part of the user-related data when a user activity-based application 146 is executed.

The processor 120 may process real-time activity state-related data in relation to the user. For example, the processor 120 may transmit the user-related data to the server 108, and the processor 120 may transmit a list of other parties similar in propensity to the user which is provided from the server 108 to another external electronic device (e.g., a wearable device) using the communication module 190.

The memory 130 may store instructions which, when executed, control the processor 120 to perform various operations. For example, the memory 130 may be built up as a database for storing the gathered user-related data.

The memory 130 may store instructions configured to, when executed, enable the processor 120 to gather data related to a first user, send a request for a user group corresponding to a first category among a plurality of categories to an external server using the communication module 190, obtain the user group corresponding to the first category based on at least part of the data related to the first user from the external server using the communication module 190, and provide information about at least one second user in the obtained user group.

The electronic device 101 may further comprise the display 212 which is viewed through part of the housing. The memory 130 may be configured to store an application based on the first user's activity.

The instructions may be configured to enable the processor 120 to output the information about the at least one second user on the display 212 when the electronic device executes an application based on the first user's activity.

The instructions may be configured to enable the processor 120 to receive a selection of a second category different from the first category, obtain a user group corresponding to the second category in response to receiving the selection, and output information about at least one third user in the obtained user group on the display 212.

The instructions may be configured to enable the processor 120 to quantify the gathered first user-related data corresponding to each data type and provide the first user-related data quantified per data type to the external server 108 using the communication module 190.

The user group corresponding to the first category may be obtained based on at least part of data associated with the first category of the first user-related data quantified per data type.

The electronic device 101 may be configured to gather the first user-related data using at least one sensor included in the sensor module 176.

The instructions may be configured to enable the processor 120 to receive the first user-related data from an external electronic device using the communication module and transmit the information about the at least one second user to the external electronic device using the communication module 190.

The first user-related data may include a plurality of data types, and wherein the plurality of data types include at least one of personal information, competition information, activity information, environment information, diet information, sleep information, service use, or use of an external electronic device related to the user.

The server 108 may include a processor 520, a memory 530, and a communication module 590 for performing communication with at least one external electronic device (e.g., the user's electronic device 101 or a wearable device 300). The server 108 may be implemented as a mobile device, such as the electronic device 101 or may be implemented as a cloud server or integrated platform on a wired/wireless network.

The processor 520 may receive user-related data from a plurality of clients (or a plurality of electronic devices) using the communication module 590. The user-related data transferred from the plurality of clients may be big data which has a high-volume and a multi-dimensional feature. The processor 520 may obtain the user-related data for each of the plurality of clients in real-time and perform clustering per category based on the obtained data. The data clustered per category may be built up into a database using the memory 530.

The memory 530 may store data obtained per user and store cluster information based on the user-related data.

The memory 530 may store per-category cluster information about all users. Thus, the users may receive the per-category cluster information from the server 108. Here, the cluster information may include at least one of the frequency of data updated by a user in a category, the number of participants in a category, a list of other parties recommended in a category, and category descriptions.

The memory 530 may be operatively connected with the communication module 590 and the processor 520.

The memory 530 may store instructions configured to, when executed, enable the processor 520 to receive data related to a first user of the external electronic device (e.g., the user's electronic device 101 or the wearable device 300) from the external electronic device using the communication module 590, receive a request for a user group corresponding to a first category among a plurality of categories from the external electronic device (e.g., the user's electronic device 101 or the wearable device 300) using the communication module 590, obtain the user group corresponding to the first category based on at least part of the first user-related data, in response to the reception of the request, and provide information about at least one second user in the obtained user group to the external electronic device using the communication module 590.

The information about the at least one second user may be displayed on a display of the external electronic device when the external electronic device executes an application based on the first user's activity.

The instructions may be configured to enable the processor 520 to obtain user groups corresponding to each of the plurality of categories, respectively, based on the at least part of the first user-related data, in response to the reception of the request and provide the user group corresponding to each of the plurality of categories to the external electronic device using the communication module 590.

The instructions may be configured to enable the processor 520 to identify the at least part of the first user-related data corresponding to the first category, cluster the identified data by applying a feature extraction model to the identified data, and identify the user group corresponding to the first category based on at least part of the clustered data.

The instructions may be configured to enable the processor 520 to identify a user group closest to the first user based on the at least part of the clustered data. The feature extraction model may be a principal component analysis (PCA).

FIG. 6 is a view 600 illustrating an example table of classifying user-related data according to a plurality of data types, according to an embodiment.

The electronic device 101 may classify user-related data into a plurality of data types as shown in the table of FIG. 6 and gather user-related data at a frequency predetermined for each data type.

Referring to FIG. 6, a data type is referred to as a sector, and the table may be constituted of sector ID 610, sector name 620, frequency 630, and factor 640. For example, when the sector ID is "SID-1" and the sector name is "user information" in a first row 611, the frequency may include the case where user personal information is input and the case where the user's body information is input, and the factor may include at least one of age, gender, height, weight, and country. For example, the country where the user is using the electronic device 101 may be identified using the ISO country code or location information.

When the sector ID is "SID-2" and the sector name is "competition information" in a second row 612, the frequency may include the case where the competition is ended, and the factor may include at least one of winning rate, tie when ended normally, or tie when competition is abandoned.

When the sector ID is "SID-3" and the sector name is "activity information" in a third row 613, the frequency may indicate that the data may be gathered at daily average, daily maximum, average per weekday, maximum per weekday, average per period of time, or maximum per period of time, and the factor may include at least one of moving time, moving distance, calorie consumption, moving distance on ascent, moving distance on descent, altitude, strength of exercise, heartrate, blood sugar, blood pressure, or kind of exercise. For example, when the data is measured every hour for 24 hours and 11 factors are provided, the total number of the factors may be 24*11.

FIG. 6 illustrates an example in which the total number of the factors is 32*11 which means 32 measurements are performed on each of eleven factors. The strength of exercise and the strength defined per type of exercise may be used. The data per weekday may be data for each weekday from Monday to Sunday. The data per period of time may be a quantified value for each of the eight periods of time which is constituted of three hours. An integer identifier (ID) may be assigned per type of exercise, and it is a quantified value for the type ID of the exercise which the user primarily did per period. For example, the strength measurement may be varied depending on walking or running, and values quantified based on the table defining exercise strengths depending on exercise types (e.g., the metabolic equivalents (MET) which are the units of display of exercise strengths) may be transmitted to the server 108.

When the sector ID is "SID-4" and the sector name is "environment information" in the fourth sector 614, the frequency may indicate that the data may be gathered at the daily average, average of the last seven days, average of the last 30 days, average of the last 180 days, or average of the last 180 days, and the factor may include at least one of temperature, humidity, air pressure, or rainfall. For example, the factor corresponding to the environment information may be obtained from the third party device or service provider.

When the sector ID is "SID-5" and the sector name is "diet information" in the fifth row 615, the frequency may indicate that the data may be gathered at the daily average, daily maximum, average per weekday, maximum per weekday, average per period of time, or maximum per period of time, and the factor may include at least one of intake calorie, water, or caffeine. For example, the factor "water" may be quantified by multiplying by 250 milliliters (ml) as a water cup unit, and the factor "caffeine" may be quantified by multiplying by 800 as a caffeine unit.

When the sector ID is "SID-6" and the sector name is "sleep information" in the sixth row 616, the frequency (i.e., gathering frequency) may indicate that the data may be gathered at the daily average, daily maximum, average per weekday, maximum per weekday, or maximum per period of time, and the factor may include at least one of sleep time and sleep quality. The sleep quality may be divided in levels from level 1 to level 4 and may be quantified. The sleep quality may be estimated by the sensor module (e.g., a photoplethysmography (PPG) sensor) of the wearable device which the user is wearing while sleeping. The heart rate (HR) or HR variability (HRV) features may be obtained by the PPG sensor. The electronic device 101 may divide the sleep state from the start of sleep to the end of sleep into four sleep stages, such as wake, rapid eye movement (REM) sleep, light sleep, and deep sleep, based on at least one of the HR feature and the HRV feature.

When the sector ID is "SID-7" and the sector name is "service use" in the seventh row 617, the frequency may indicate that the data may be obtained at the daily average, daily maximum, average per weekday, maximum per weekday, average per period of time, or maximum per period of time, and the factor may include application use time. The application use time may be quantified in seconds.

When the sector ID is "SID-8" and the sector name is "third party device" in the eighth row 618, the frequency may indicate that the data may be obtained at the daily average, daily maximum, average per weekday, maximum per weekday, average per period of time, or maximum per period of time, and the factor may include at least one of a use time of a watch (e.g., the wearable device 300) and a cadence use time. The use time may be quantified in seconds.

Since the components corresponding to each sector need to be quantified, they may be quantified by referencing the table of FIG. 6, and the units for quantification are not limited thereto but may rather be adjusted considering the user's life pattern. However, such factors as country and type of exercise may be given unique integer IDs for quantification, and the strength of exercise may be quantified based on the MET which defines strengths based on calorie consumptions according to the type of exercise.

The electronic device 101 may identify the data type of the user-related data based on the sensor data and, when the reference defined in the gathering frequency is met, transmit it to the server 108. The electronic device 101 may perform control to obtain user-related data when a preset reference is met or at the request of the server 108. In this case, the preset reference may be the gathering frequency and such a setting may be made that the data is transmitted to the server 108 in a particular period.

The electronic device 101 may gather user-related data including at least one of the user information, competition information, activity information, environment information, diet information, sleep information, service use, or third party device use by referring to the table of FIG. 6 and create the data into a database. The electronic device 101 may calculate indexes for quantifying data per data type and create them into a database.

Although in the above example the user-related data is classified into eight sectors (or data types), there may be about 700 factors or more which influence the user's health and life pattern and, thus, more sectors may be added without being limited to those shown in FIG. 6.

Figure 7:
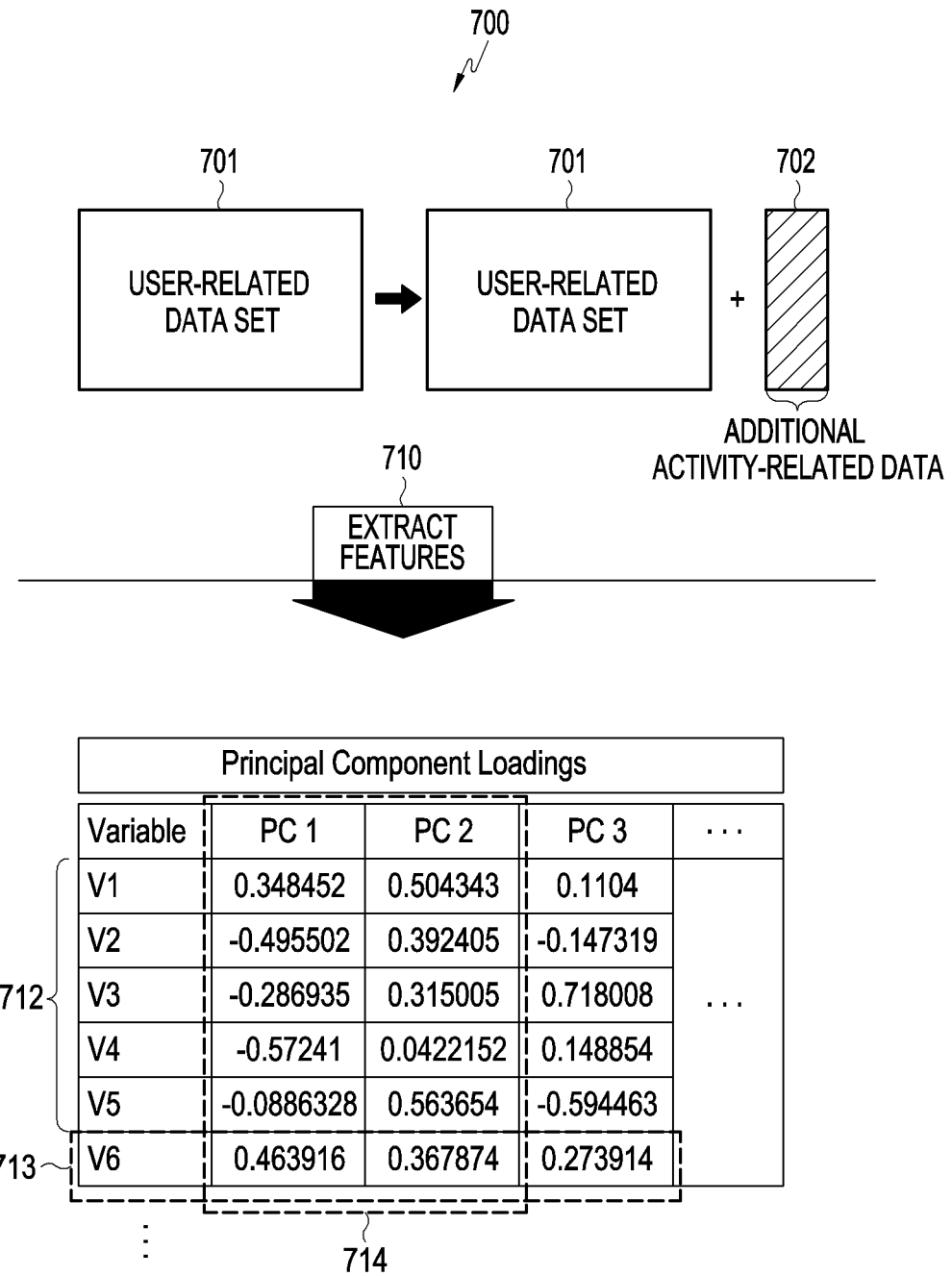
FIG. 7 is a view illustrating a method of applying a learning model as a variable is added, according to an embodiment.

FIG. 7 is a view 700 illustrating a method of applying a learning model as variables are added, according to an embodiment.

Referring to FIG. 7, the server 108 gathers a user-related data set 701 from a plurality of clients. The user-related data used for learning in the server 108 may be classified to be suited for each feature and may be learned (i.e., obtained) in real-time. The user-related data set 701 may mean the values 712, such as V1, V2, V3, V4, and V5, obtained by quantifying the user-related data. For example, in a case where the quantified value of sleep quality is V1, the quantified value of strength of exercise is V2, the quantified value of environment information is V3, the quantified value of application use time is V4, and the quantified value of diet information is V5, if new user-related data is added as a new sensor function is added, the quantified value of the newly added data may be denoted as V6.

As set forth above, the user-related data used for learning may be newly added corresponding to a new sensor function or various healthcare items (e.g., calorie consumption, sodium reduction, or weight loss). The user-related data may be at least partially varied corresponding to the user's activity. For example, at least some of the pieces of user-related data, e.g., V1, V2, V3, V4, and V5 may be changed into V1', V2', V3', V4', and V5'. Since sectors for classifying the user-related data may be added as necessary, additional activity-related data 702 (e.g., V6) may dynamically be added to the user-related data (e.g., V1, V2, V3, V4, and V5) as shown in FIG. 7. The additional activity-related data 702 may be data corresponding to the added sector or newly gathered data according to the new sensor function. The user-related data 701 and the additional activity-related data 702 may be used to search for other parties which are most similar in propensity, e.g., health or activity pattern, to a particular user. The user-related data 701 and the additional activity-related data 702 are values quantified in the electronic device 101 and, thus, may be represented as quantified values 712 and 713 (e.g., V1, V2, V3, V4, V5, and V6) as shown in FIG. 7. Although FIG. 7 illustrates six quantified values, a few tens or a few hundreds of quantified values may be present since all data quantifiable among the pieces of user-related data may be used for learning. For example, the quantified values 713 (e.g., V6) representing the additional activity-related data 702 may be added in real-time to the quantified values 712 (e.g., V1, V2, V3, V4, and V5) representing the user-related data 701. Here, the quantified values (e.g., V1, V2, V3, V4, V5, and V6) may be denoted variables.

The server 108 may learn all the user-related data 701 and 702 in real-time and extract features 710. When the PCA is used as the feature extraction scheme, as many principal components (PCs) as the number of variables may be extracted. For example, when the number of variables is n (e.g., V1, V2, V3, V4, V5, V6, . . . , Vn), a total number of n network primary components (e.g., PC1, PC2, PC3, PC4, PC5, PC6, . . . , PCn) may be extracted. As such, if upper primary components (e.g., PC1 and PC2) 714, which are to be used actually for clustering, are selected from among the multi-dimensional primary components (e.g., PC1, PC2, PC3, PC4, PC5, PC6, . . . , PCn), it may then be possible to effectively classify the features for the user-related data according to designated references (e.g., categories). Although such an example has been described where the upper two primary components (e.g., PC1 and PC2) 714 among the multi-dimensional primary components are used and the dimension is reduced to two dimensions, it may also be possible to extract features, with the dimension reduced to three dimensions by using the three upper primary components (e.g., PC1, PC2, and PC3). By so doing, the server 108 may distribute the user-related data according to the categories. The server 108 may cluster users per category and build up a database therefor.

The categories may be ones for classifying the user's life patterns and may include at least one of lifestyle, exercise pattern, environment, sleep pattern, food style, service use pattern, body mass index (BMI), and third party device use. The user-related data 701 and the additional activity-related data 702 may be used for independently creating a new category or learning each category according to data types. The categories may be produced by the server 108, and information about the modified or newly added category may be transferred from the server 108 to each electronic device. Thus, categories reflecting the latest trend may be provided without unnecessary loads for applying information about modified or new categories in each electronic device.

Figure 8A:
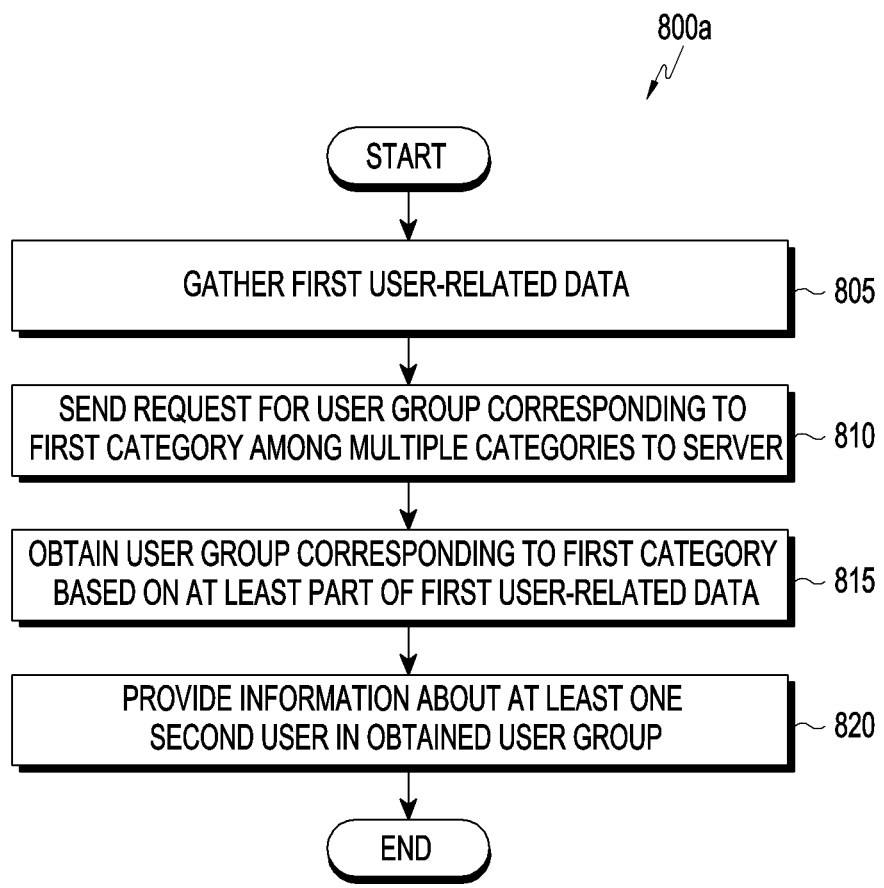
FIG. 8A is a flowchart illustrating operations of an electronic device for providing a recommendation service based on user-related data, according to an embodiment.

FIG. 8A is a flowchart 800a illustrating operations of an electronic device to provide a user-related data-base recommendation service, according to an embodiment. The method includes steps 805, 810, 815, and 820. Each step operation of the method may be performed by at least one of an electronic device or at least one processor of the electronic device. At least one of steps 805, 810, 815, and 820 may be omitted, some operations thereof may be performed in reverse order, or other operations may be added thereto.

The electronic device gathers data related to a first user in step 805. For example, the first user may be the user of the electronic device, and the first user-related data may consist of a plurality of data types and may include at least one of user personal information, competition information, activity information, environment information, diet information, sleep information, service use information, or external electronic device use information. The electronic device may quantify the gathered first user-related data corresponding to each data type and provide the server with the first user-related data quantified per data type.

In step 810, the electronic device sends a request for a user group corresponding to a first category among a plurality of categories to the server. For example, the electronic device may receive a selection of the first category among the plurality of categories. Unless the user selects any one category, the electronic device may send a request for user groups for all categories or a preset category when an application based on the first user's activity is executed.

In step 815, the electronic device obtains the user group corresponding to the first category based on at least part of the first user-related data. The user group corresponding to the first category may be one obtained based on at least part of the data associated with the first category of the first user-related data quantified per data type. For example, the selection of the user group corresponding to the first category may be performed by the server, and the server may use at least part of the first user-related data for user group selection.

In step 820, the electronic device provides information about at least one second user in the obtained user group. The information about the at least one second user may be output on the display of the electronic device. The screen displaying the information about the at least one second user may be displayed on the electronic device according to a request for executing a designated application, e.g., the first user activity-based application. The screen may also be displayed on the electronic device regardless of whether the request for executing the application is received (i.e., automatically). When the electronic device connects to an external electronic device (e.g., the wearable device 300), the electronic device may provide the information about the at least one second user to the external electronic device so that the information may be displayed on the display of the external electronic device. For example, the at least one second user may be competitors with the first user, who are most similar in user activity according to the first user's various interests, abrupt ambient variations, or changes in the exercise record.

As set forth above, a user interface for providing information about competitors who are most similar in activity type to the user and may thus compete with the user may be provided, thereby providing health information and healthcare results for the user along with a motive for maintaining good health.

Figure 8B:
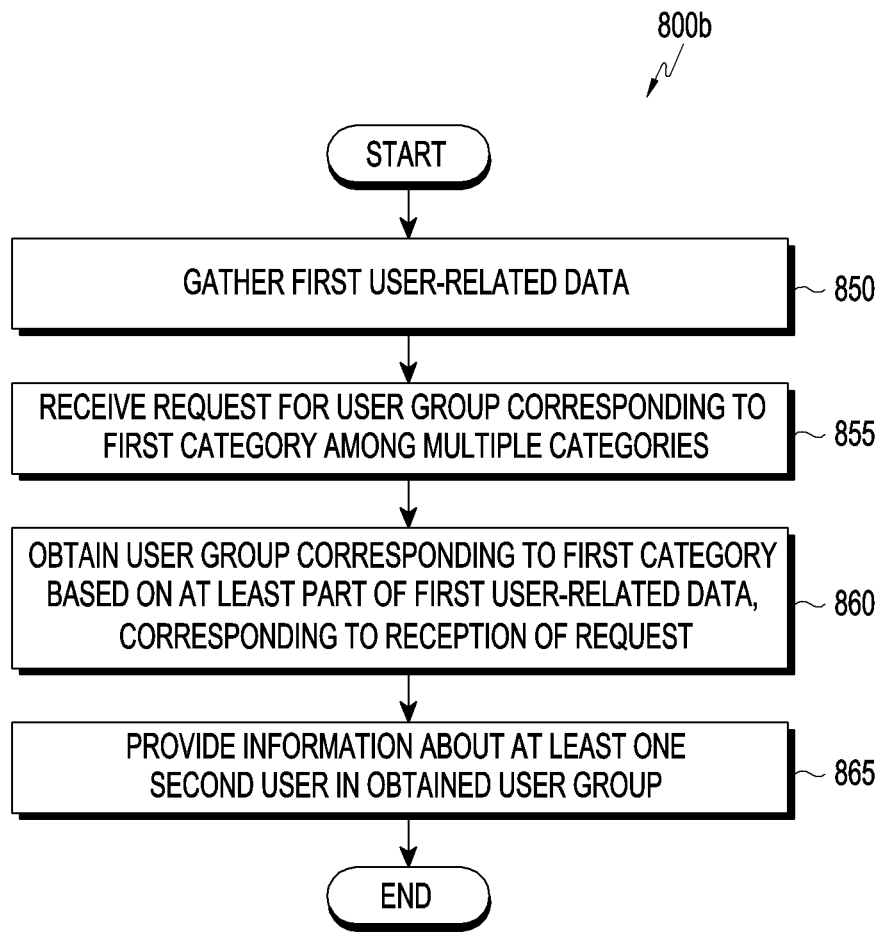
FIG. 8B is a flowchart illustrating operations of a server for providing a recommendation service based on user-related data, according to an embodiment.

FIG. 8B is a flowchart 800b illustrating operations of a server for providing a user-related data-based recommendation service, according to an embodiment. The method include steps 850, 855, 860, and 865. Each step/operation of the method may be performed by an electronic device (e.g., the server 108) or at least one processor 502 of the electronic device. At least one of steps 850, 855, 860, and 865 may be omitted, some operations thereof may be performed in reverse order, or other operations may be added thereto. The electronic device of FIG. 88 may denote a server.

The server gathers the first user-related data in step 850. The server may gather the user-related data from the electronic devices of a plurality of users which are a plurality of clients. The first user-related data may be data quantified per data type by the electronic device, and the server may classify and process user-related data based on category learning models whenever the user-related data is received, which is described below in connection with FIG. 9.

In step 855, the server receives a request for a user group corresponding to a first category among a plurality of categories. For example, the server may receive the request from the first user's electronic device while gathering the user-related data from the plurality of clients.

In step 860, the server obtains the user group corresponding to the first category based on at least part of the first user-related data. The server may identify at least part of the first user-related data corresponding to the first category, cluster the identified data by applying a feature extraction model to the identified data, and identify the user group corresponding to the first category using the clustered data. The server may identify the user group closest in distance to the first user using the clustered data. As an example of the feature extraction model, PCA may be used. The feature extraction model may be a scheme for extracting features by which the users may be distinguished per category and may reduce the multi-dimensional information about the users into a lower dimension (e.g., two dimensions).

In step 865, the server provides information about at least one second user in the obtained user group. The obtained user group may be the user group closest in position to the first user among the plurality of user groups corresponding to the first category.

As set forth above, embodiments of the disclosure may encourage the user's desire for maintaining good health and using the healthcare service.

Figure 9:
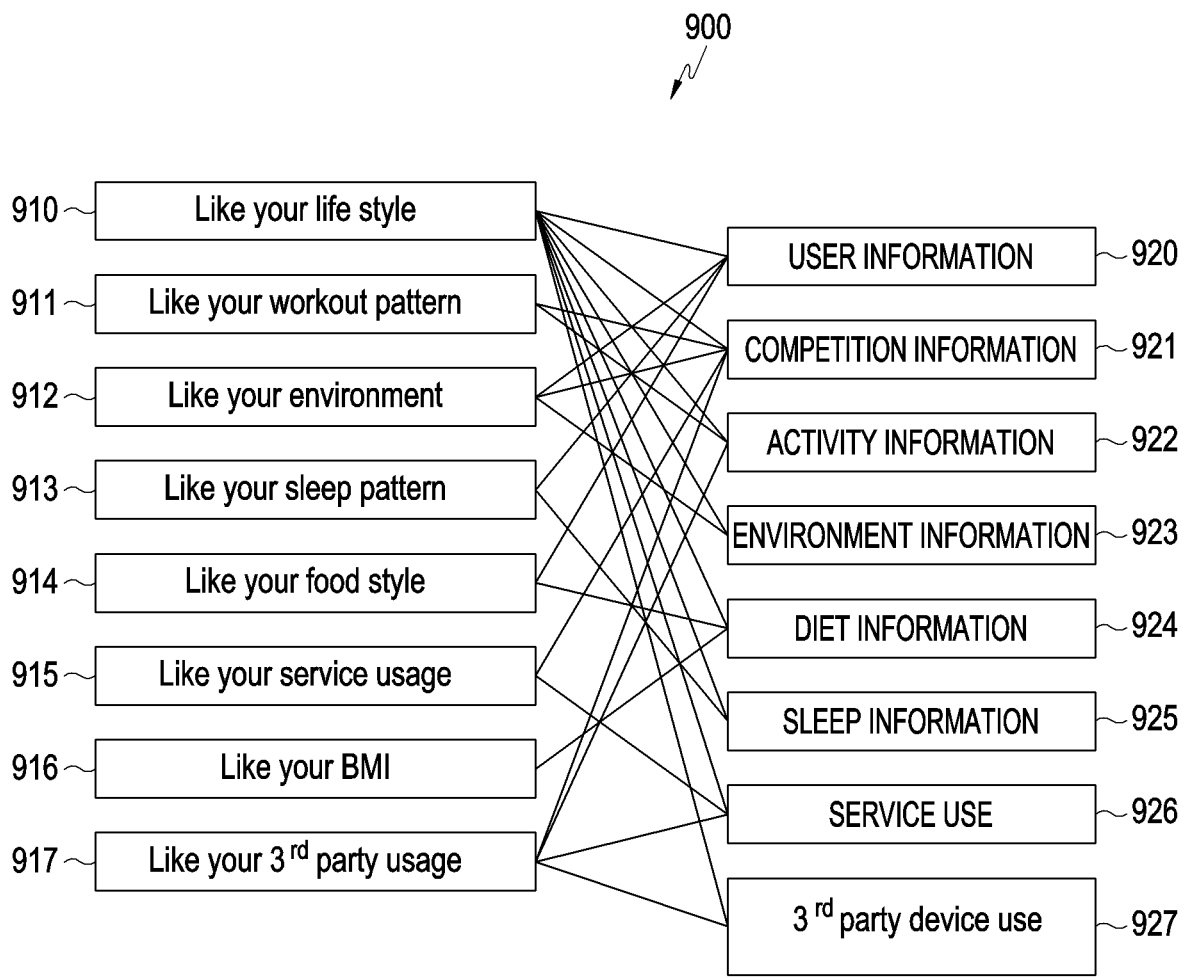
FIG. 9 is a view illustrating an example relationship between categories and user-related data, according to an embodiment.

FIG. 9 is a view 900 illustrating an example relationship between categories and user-related data, according to an embodiment.

FIG. 9 shows an example relationship as to what combination of data types 920, 921, 922, 923, 924, 925, 926, and 927 is considered for each category 910, 911, 912, 913, 914, 915, 916, and 917.

The first category "like your lifestyle" 910 (i.e., lifestyle) may be one based on all types of activities of the user and, for the first category "like your lifestyle" 910, all data types 920, 921, 922, 923, 924, 925, 926, and 927 of user-related data may be used. For the categories other than the first category, one data type of the user-related data or a combination of two or more data types may be used.

For the second category "like your workout pattern" 911 (i.e., exercise pattern), a combination of data type 922 corresponding to activity information and data type 921 corresponding to the competition information of the user-related data may be used. For example, users with similar activity patterns may be obtained by applying quantified values, i.e., exercise-related variables, of the data type 922 corresponding to the user's activity information.

For the third category "like your environment" 912 (i.e., environment), a combination of the data type 920 corresponding to the user information and the data type 923 corresponding to environment information may be used. For example, as environmental variables may apply to the third category "like your environment" 912, such information as temperature, humidity, air pressure, or rainfall may be used so that similar values may be obtained for users who are influenced by environmental variations or for users who enjoy seasonal sports or particular weather conditions.

For the fourth category "like your sleep pattern" 913 (i.e., sleep pattern), a combination of the data type 920 corresponding to user information and the data type 925 corresponding to sleep information may be used.

For the fifth category "like your food style" 914 (i.e., food style), a combination of the data type 920 corresponding to user information and the data type 924 corresponding to diet information may be used. For example, for the categories "like your sleep pattern" 913 and "like your food style" 914, variables associated with diets or sleep patterns may be taken into consideration. Thus, users who have similar diets or sleep patterns may share feelings with each other via the social network and enhance their sleep quality and healthful diets while competing with each other by engaging in healthier sleep and diet habits.

For the sixth category "like your service usage" 915 (i.e., service use pattern or application use pattern), a combination of the data type 920 corresponding to user information and the data type 926 corresponding to service use (ex: application use) may be used. For example, for the category "like your service usage" 915, the use pattern for use of the service may be taken into consideration. As such, since user-related data is created and updated according to the service use pattern, users who have similar service use patterns may compete with each other.

For the seventh category "like your BMI" 916 (i.e., BMI), the data type 924 corresponding to diet information may be used. For example, the user may receive a recommendation for similar users based on his or her BMI as the primary component.

For the eighth category "like your $3^{rd}$ party usage" 917 (i.e., third party device use), a combination of the data type 921 corresponding to user-related data competition information, the data type 922 corresponding to activity information, the data type 926 corresponding to service use, and the data type 927 corresponding to third party device use may be used. For example, if there is a user who uses a third party device with the third party device attached to a bicycle, a difference may be made in activity record or service use frequency depending on the type of electronic device as compared with users who do not use the third party device. Thus, for the category "like your $3^{rd}$ party usage" 917, a combination of associable data types, e.g., the data type 921 corresponding to the competition information of user-related data, the data type 922 corresponding to activity information, the data type 926 corresponding to service use, and the data type 927 corresponding to third party device use may be considered together.

Figure 10:
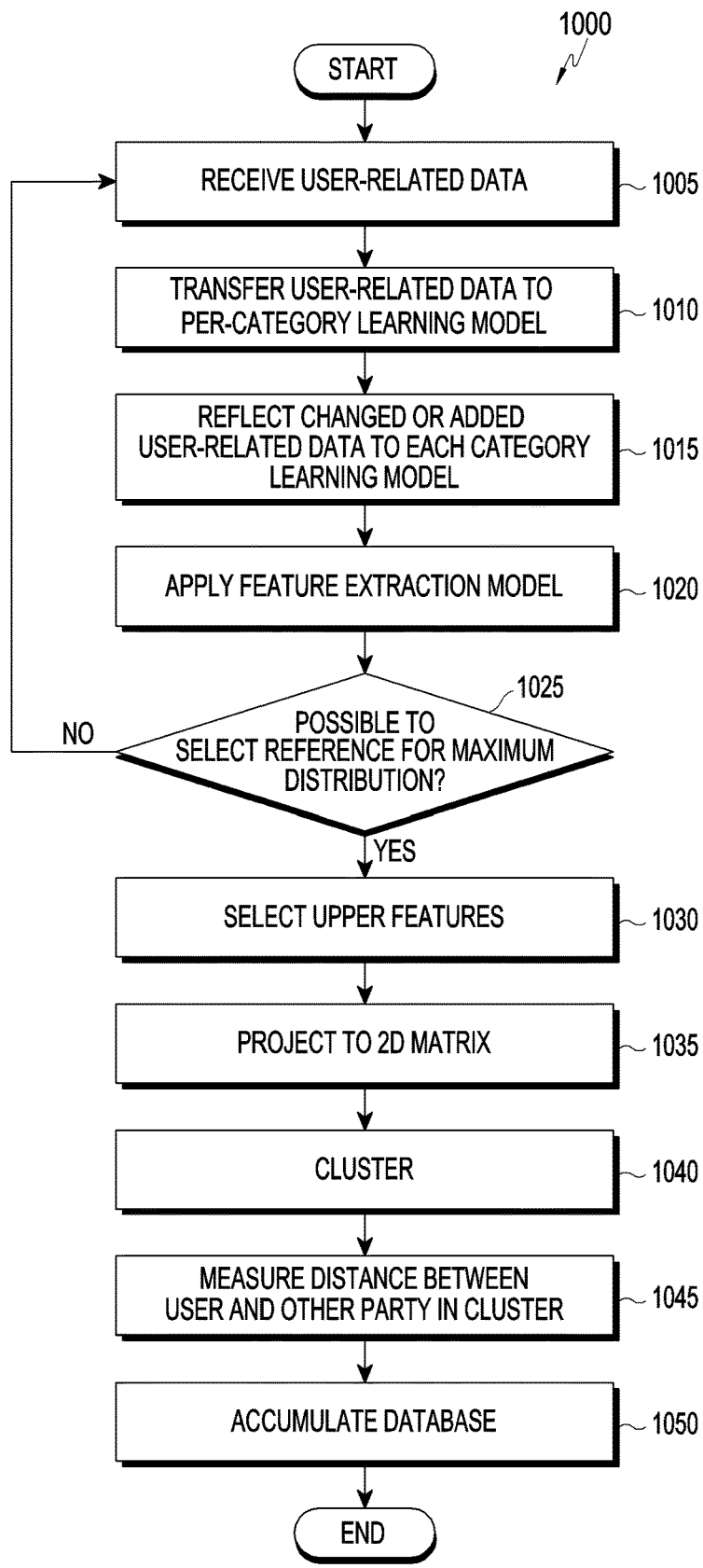
FIG. 10 is a flowchart illustrating, in detail, a series of steps pertaining to an order of operation of FIG. 8B, according to an embodiment.

FIG. 10 is a flowchart 1000 illustrating, in detail, a series of steps pertaining to an order of operation of FIG. 8B. The method includes steps 1005, 1010, 1015, 1020, 1025, 1030, 1035, 1040, 1045, and 1050. Each step/operation of the method may be performed by an electronic device (e.g., the server 108) or at least one processor 502 of the electronic device. According to an embodiment, at least one of steps 850, 855, 860, and/or 865 may be omitted, some operations thereof may be performed in reverse order or other operations may be added thereto. The electronic device of FIG. 8B and FIG. 10 may denote a server.

In step 1005, the server receives user-related data from a plurality of electronic devices.

In step 1010, the server transfers the received user-related data to a per-category learning model. For example, it may be transferred to the per-category learning model using at least one or a combination of two or more of the data types of the user-related data.

In step 1015, the server reflects changed or added user-related data to each category learning model. For example, user-related data changed or added in real-time may be added in the scheme shown in FIG. 7. In step 1020, the server applies a feature extraction model to at least part of the user-related data transferred per category. As the feature extraction model, a PCA scheme may be used. The PCM scheme is a method for efficiently summarizing multi-dimensional data which has correlations between variables into lower-dimensional data. The use of the PCA scheme may reduce the number of dimensions of the users' multi-dimensional information into lower-dimensional information (e.g., two-dimensional information).

By applying the feature extraction model, a distribution of user-related data may be known. The server determines whether a reference for the maximum distribution may be selected in step 1025. Specifically, referring to FIG. 7, in a case where each of 100 user-related data-related variables (e.g., V1, V2, V3, . . . , V100)) are received from 100,000,000 users, it may be critical to determine references so that the features for the user-related data can be optimally distributed. The process of reducing the number of variables by analyzing the variables for user-related data to define primary components which may represent all the data may be referred to as the PCA scheme. For example, if a reference is selected by which the data may be most broadly distributed when n variables are spread in an n-dimensional space, it may be possible to distinguish and classify the features of user-related data. In other words, because many primary components for user-related data may be obtained as the number of variables upon classifying the user-related data according to a designated reference, this may simplify the data characteristics of the multi-dimensional complicated data by PCA.

If it is not possible to select a reference by which the user-related data may be classified, the server returns to step 1005 or terminate the method.

If it is possible to select a reference for classifying the user-related data, the server selects upper features (or upper primary components) in step 1030. For example, if as many primary components may be obtained as the number of the variables, and the uppermost two primary components (e.g., PC1 and PC2) are selected from among the plurality of primary components, a distribution graph is created and projected to the two-dimensional matrix in step 1035. Projecting to the two-dimensional matrix may mean obtaining a first primary component and a second primary component through PCA and representing them in a two-dimensional point graph.

As such, as the upper features are selected, the server may create a distribution graph based on the upper features. As set forth above, the upper, e.g., two or three, features which show the largest data distribution per category may be extracted by applying the feature extraction model to the user-related data transferred per category, and the database may be updated with the distribution degree (value) of the extracted features. The server performs user clustering using the distribution graph in step 1040. The server measures the distances between the user and other parties in the cluster in step 1045.

For example, another party closest in distance to the user may be a competitor meaningful to the user, and other parties far away from the user may not be competitors meaningful to the user. For example, when the user resides in a first city, other parties in the first city may be meaningful competitors, and other parties residing in a second city of another country may not be meaningful competitors since they reside in a different city and a different country. Thus, the server may use the measured distances to provide at least one other party closest to the user. The server accumulates, in the database, user-related data including measurement information between other parties and the user in the cluster in step 1050. As set forth above, because the distances between the user and other parties are previously stored, the server may provide a list of competitors in an order of the other parties that are closest to the user when providing a response to a request for competitors from the electronic device in the future.

The operation of applying the feature extraction model and then clustering is described below in connection with FIG. 11.

Figure 11:
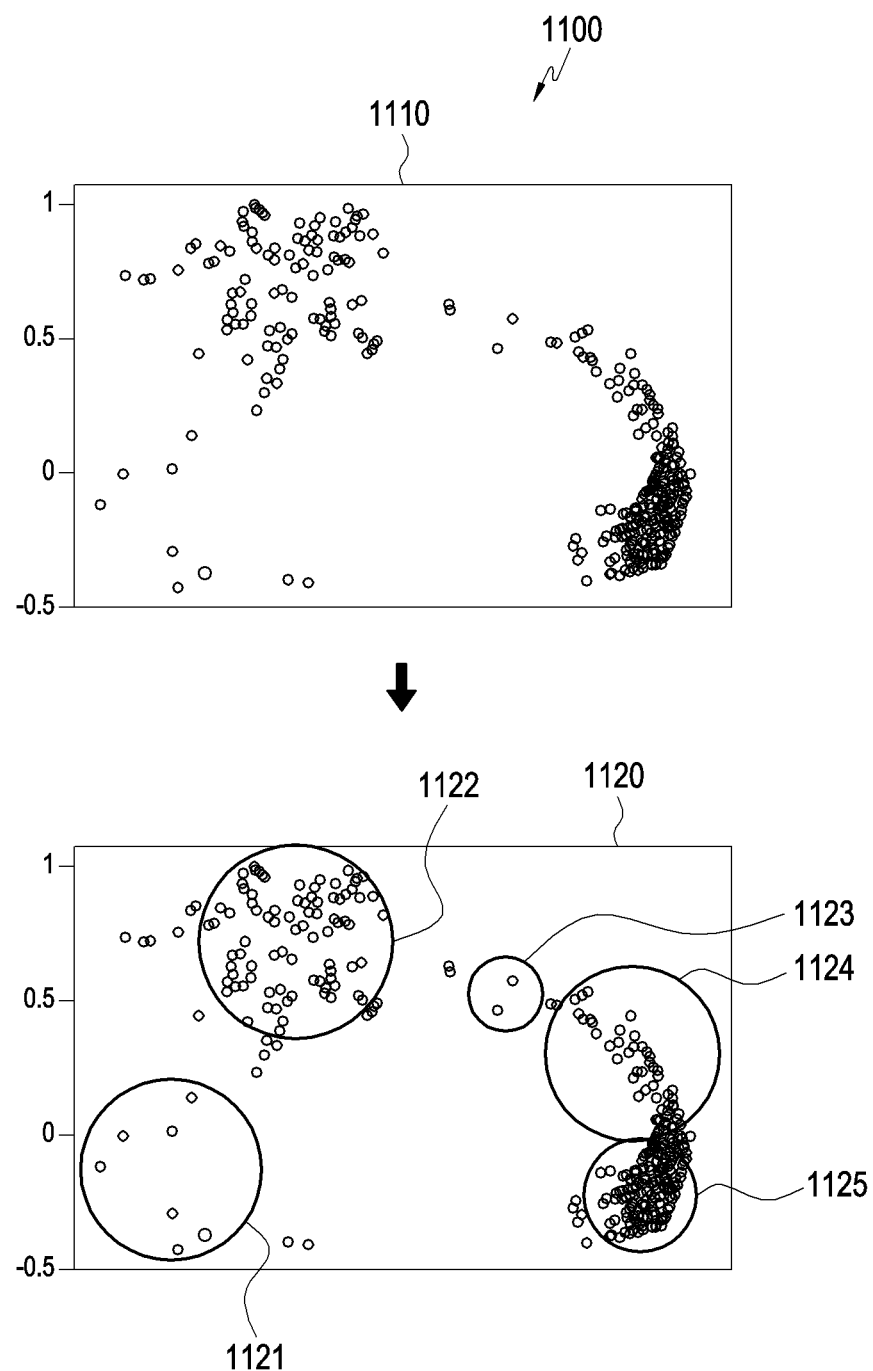
FIG. 11 is a graph illustrating two-dimensional (2D) matrix projection and clustering, according to an embodiment.

FIG. 11 is a graph 1100 illustrating projection into a two-dimensional matrix and clustering, according to an embodiment.

Referring to FIG. 11, a two-dimensional matrix 1110 for the user may be obtained using upper features (or upper primary components), e.g., two features (e.g., PC1 and PC2). FIG. 11 illustrates a distribution of user-related data in the two-dimensional matrix 1110, and a plurality of clustering results 1121, 1122, 1123, 1124, and 1125 may be obtained from the distribution 1120 of features. As such, clustering enables inter-user distribution for the most similar feature. The server may perform clustering using a clustering algorithm, such as the K-means algorithm.

Figure 12:
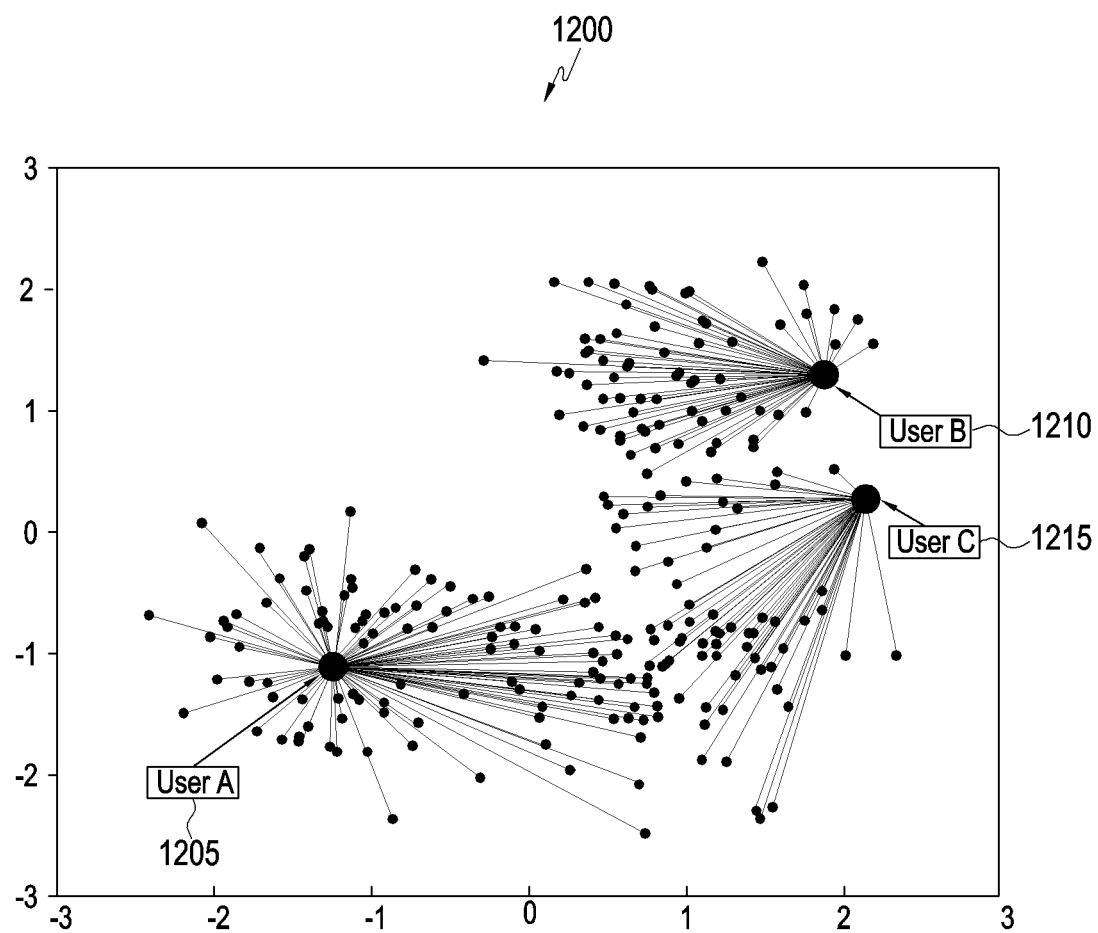
FIG. 12 is a view illustrating inter-user similarity measurement, according to an embodiment.

FIG. 12 is a view 1200 illustrating a measurement of inter-user similarity, according to an embodiment.

Referring to FIG. 12, the user-related data projected to the two-dimensional matrix as shown in FIG. 11 may have such a form that pieces of data for users with strong similarity per category come together. In this case, the server may calculate the distances between users as in the distribution for users A 1205, B 1210, and C 1215, and may previously store them in the database. Thereafter, upon receiving a request for competitors from a particular user, the server may sort and provide competitors in an order based on how close each user is to the particular user in response to the request. For example, since the closest user may be most similar to the requesting user, and the farthest user may be the most different from the user, the server may provide information about at least one other party (i.e., user) closest to the requesting user.

Figure 13A:
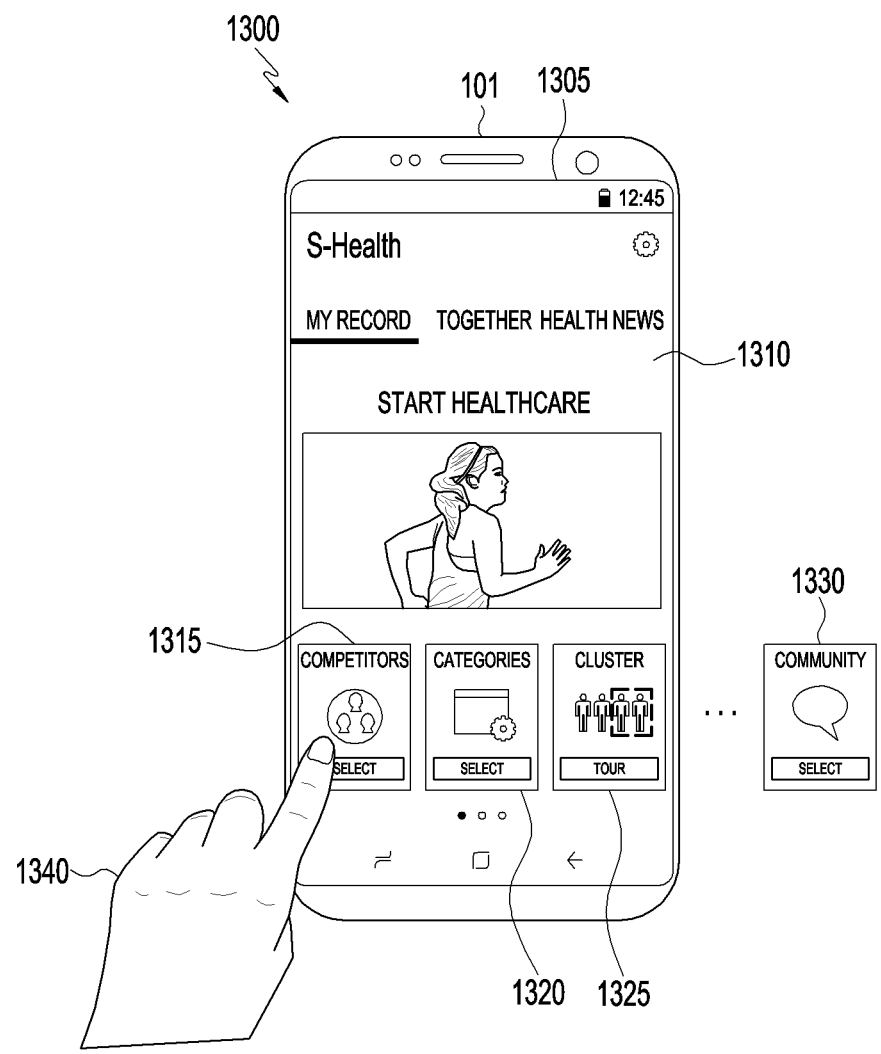
FIG. 13A is an example view illustrating a screen of providing a service based on a user's activity on an electronic device, according to an embodiment.

FIG. 13A is a view 1300 illustrating an example screen for providing a user activity-based service on an electronic device, according to an embodiment.

Referring to FIG. 13A, the electronic device 101 displays an execution screen 1310 of a user activity-based application. The user activity-based application may be an application related to the user's health, such as a healthcare application or a game challenge-related application. For example, the application for healthcare may be the S-health application.

The application execution screen 1310 may be displayed on the display 1305 of the electronic device 101 according to a designated application execution request. When the user activity-related data is obtained or updated, the electronic device 101 may display the application execution screen 1310 regardless of whether the designated application execution request is received (or the application execution screen 1310 may be displayed automatically). When the user activity-related data is obtained or updated, it may be stored in the memory 130 of the electronic device 101 without being displayed, regardless of whether the designated application is executed.

The application execution screen 1310 may display items (or interfaces) 1315, 1320, 1325, and 1330 for providing various pieces of information related to the user's activity. As shown in FIG. 13A, the application execution screen 1310 may include an item 1315 for selecting a competitor, an item 1320 for selecting a category, an item 1325 for cluster touring for moving between the group where the user belongs and other groups, and an item 1330 for identifying community-related information. As shown in FIG. 13A, the items are not limited to a particular type as long as the items may be quantified as grades or values in relation to the user, such as, e.g., weight loss, exercise distance, calorie consumption, sleep quality, or sodium intake. Thus, when the user 1340 selects items (or interfaces) 1315, 1320, 1325, and or 1330, various items for the user's healthcare may be added or modified and be displayed on the application execution screen 1310.

Figure 13B:
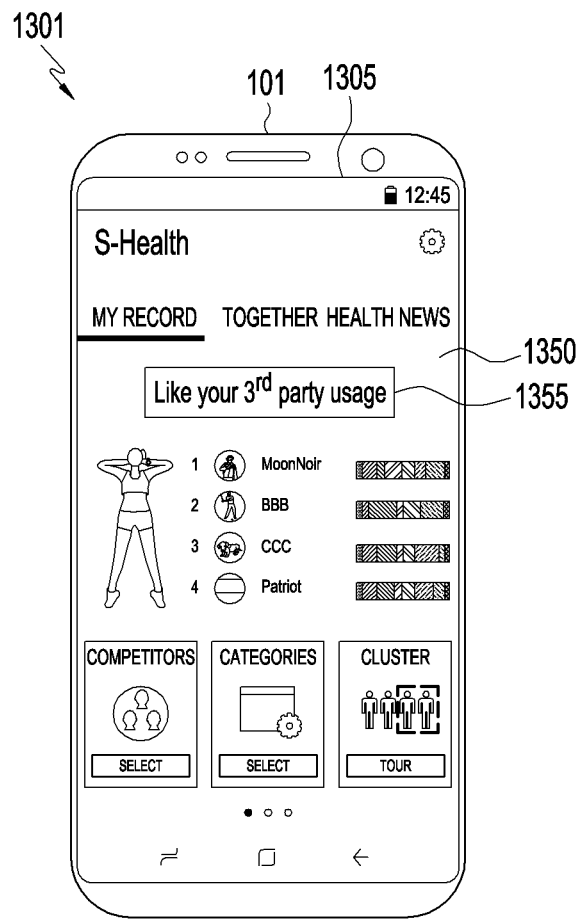
FIG. 13B is an example view illustrating a screen of providing a service according to a category of priority on an electronic device, according to an embodiment.

FIG. 13B is a view 1301 illustrating an example service providing screen according to prioritized categories, according to an embodiment.

Referring to FIG. 13B, the electronic device 101 displays a user interface 1350 based on the user's activity. Here, the user interface 1350 may be an execution screen of a user activity-based application or may be a main home screen displayed on the display 1305 regardless of whether the application is executed. The main home screen may be the first screen displayed on the display 1305 when the electronic device 101 powers on.

The user may directly change the category by selecting the item for selecting category. The user interface based on the prioritized (i.e., selected) category may be displayed according to the user's use pattern. For example, when the user uses a wearable device, the category "like your $3^{rd}$ party usage" 1355 ($3^{rd}$ party device use), which is related to use of the wearable device, may have the highest priority and, thus, the user interface 1350, according to the category "like your $3^{rd}$ party usage" 1355 ($3^{rd}$ party device use) may be displayed as shown in FIG. 13B. As such, the priority of categories may be adjusted depending on the user's activity pattern except for a first category (i.e., a lifestyle category).

When the user uses the wearable device 300, the category "like your $3^{rd}$ party usage" 1355 ($3^{rd}$ party device use) may be the category which the user is primarily interested in as shown in FIG. 13B, the user interface 1350 may include various input items for recommending competitors and information based on the category "like your $3^{rd}$ party usage" 1355 ($3^{rd}$ party device use). For example, the input items may include the item for selecting a competitor in the "like your $3^{rd}$ party usage" 1355 ($3^{rd}$ party device use) category, the item for changing the priority of category, and the item for cluster touring for moving between the group where the user belongs and other groups. For example, the user interface 1350 may display the information about the competitor the user selected or information of recommending the plurality of competitors constituting the cluster (or group).

As set forth above, the order of categories may be defined corresponding to the frequency of updating the user activity-related data and, thus, the category related to the data most frequently updated among the pieces of user activity-related data may be changed to have the highest priority. Thus, the user interface 1350 may display the information corresponding to the category of the highest priority.

Figure 14:
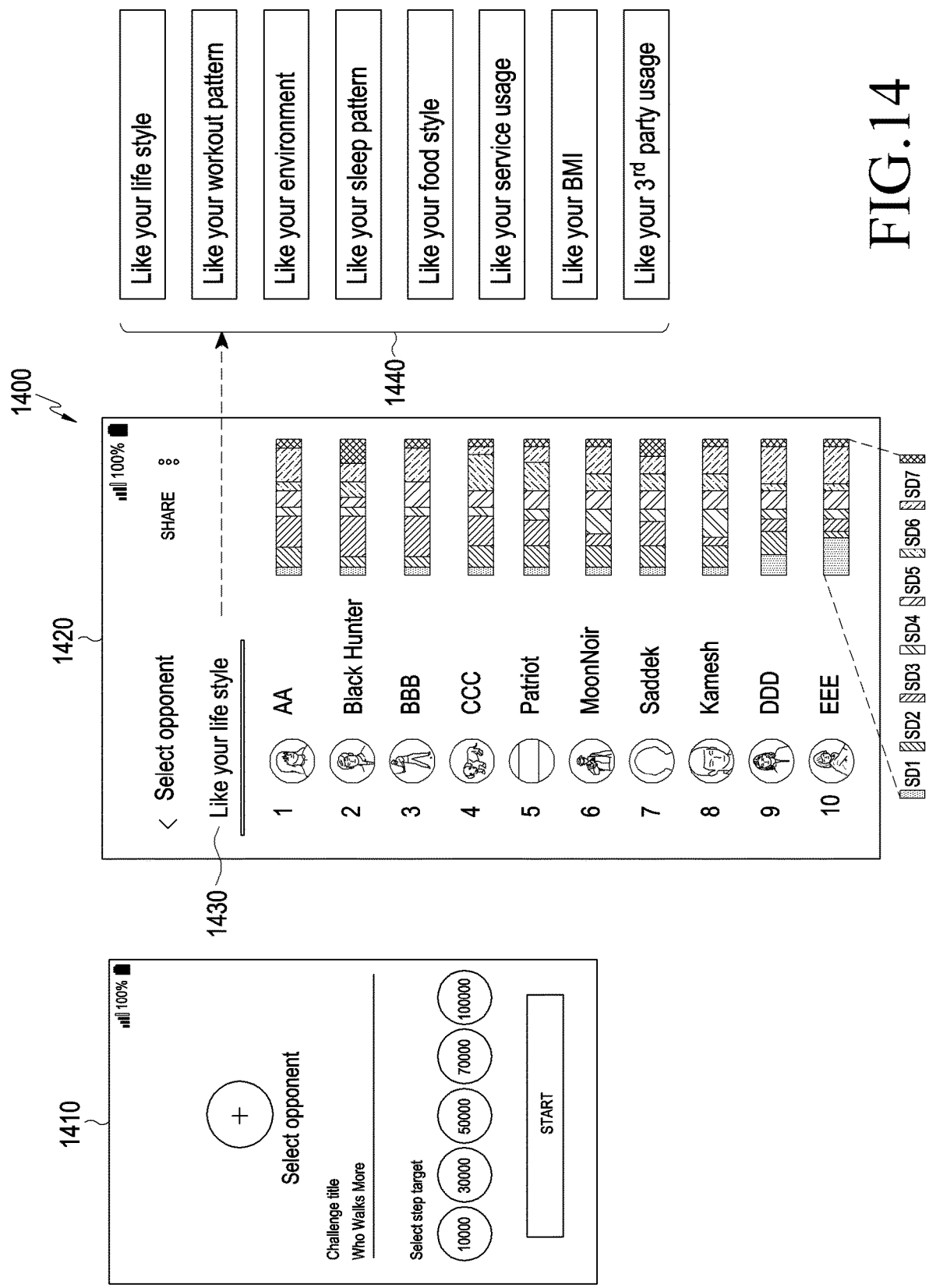
FIG. 14 is a view illustrating an example user interface outputting per-category competitor information on an electronic device, according to an embodiment.

FIG. 14 is a view 1400 illustrating an example user interface outputting per-category competitor information on an electronic device, according to an embodiment.

Referring to FIG. 14, the electronic device, upon receiving information about user group information per category, may display the per-category user group information to be intuitively compared using a graphics interface. The graphics interface may be displayed in various manners corresponding to the type of electronic device.

For example, when the user selects or browses competitors in FIG. 13A, the first screen 1410 of FIG. 14 may be displayed as the item 1315 for selecting a competitor.

The first screen 1410 may display competition-related information to be produced, e.g., information about a challenge title and challenge target (e.g., step target) and a menu for adding competitors. Other various pieces of information for competition may be produced, such as a challenge type or how to proceed with a challenge. This information may be displayed as well. A second screen 1420 may be displayed corresponding to a touch input for requesting a competitor, and the second screen 1420 exemplifies a list of at least one competitor in the user group corresponding to the first category. The user may select his or her desired category among the plurality of categories 1440 by selecting the object 1430 for category selection. The desired category may be changed by implementing the user interface to display a plurality of categories 1440 upon selecting the item 1320 for category selection of FIG. 13A. For example, when a plurality of tabs for category selection are provided, a category may be selected by selecting each tab, or category selection may also be carried out by swiping, without being limited to a particular method for category selection.

The screen corresponding to each category may list up and display competitors similar to the user. For example, the order of sorting the competitors may be implemented by referring to the data stored as the server calculates distances from the user.

The electronic device may convert the variables corresponding to the data types SD1, SD2, SD3, SD4, SD5, SD6, and SD7 corresponding to the category into percentages and display them using infographics. Accordingly, the spectrum infographics displayed per electronic device may be implemented by converting the relative value in the data type used in the category into a percentage. Since the category is "lifestyle" in the second screen 1420, portions of all the data types SD1, SD2, SD3, SD4, SD5, SD6, and SD7 of the user-related data are displayed. For example, when the category is "exercise pattern," the portions of the data types corresponding to activity information and competition of the user-related data may be displayed on the screen of the category "exercise pattern."

Categories other than the lifestyle category may be provided with the order of categories being adjusted depending on the user's pattern of use. For example, when the user uses a wearable device 300 which is of a watch type, the electronic device or the wearable device may first display the category "third party device." When the update for exercise record is more frequent than the other variables for the user, the category "exercise pattern" may be displayed first. As set forth above, since the category may be changed and adaptively displayed corresponding to the user's activity pattern, category recommendation may be performed according to the user's interest.

Figure 15:
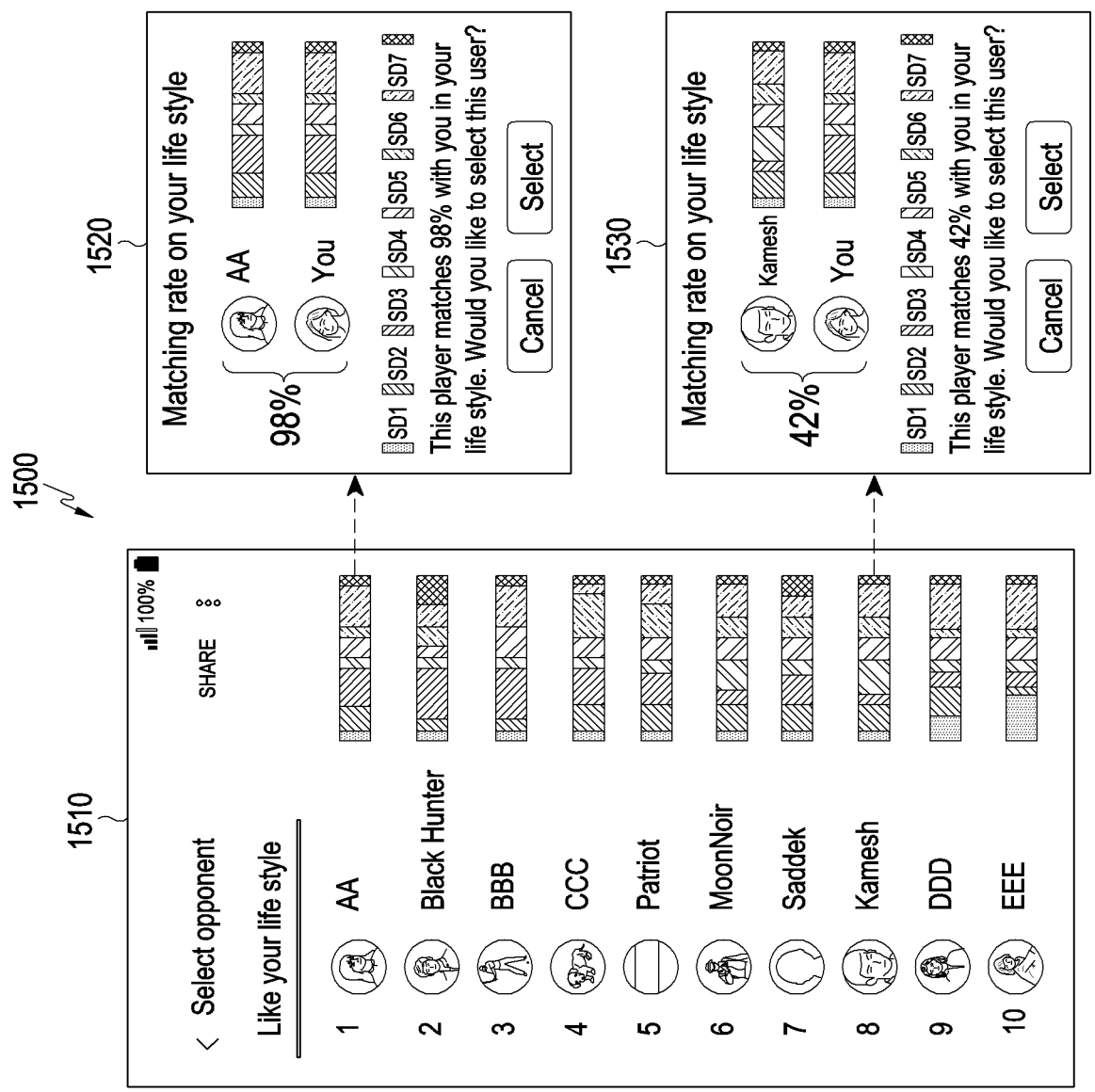
FIG. 15 is a view illustrating an example user interface outputting detailed information about per-category competitors on an electronic device, according to an embodiment.

FIG. 15 is a view 1500 illustrating an example user interface outputting detailed information about per-category competitors on an electronic device, according to an embodiment.

Referring to FIG. 15, a function may be added to enable communication with competitors sorted on the first screen 1510. For example, a function for one-to-one competition or chatting for building a social network with competitors may be provided corresponding to a user's request. When a competitor is selected from the list of competitors on the first screen 1510, screens 1520 and 1530 providing detailed information about the competitor may be displayed. The user may compare his or her information and other parties' information at a glance through the detailed information screens 1520 and 1530.

Figure 16:
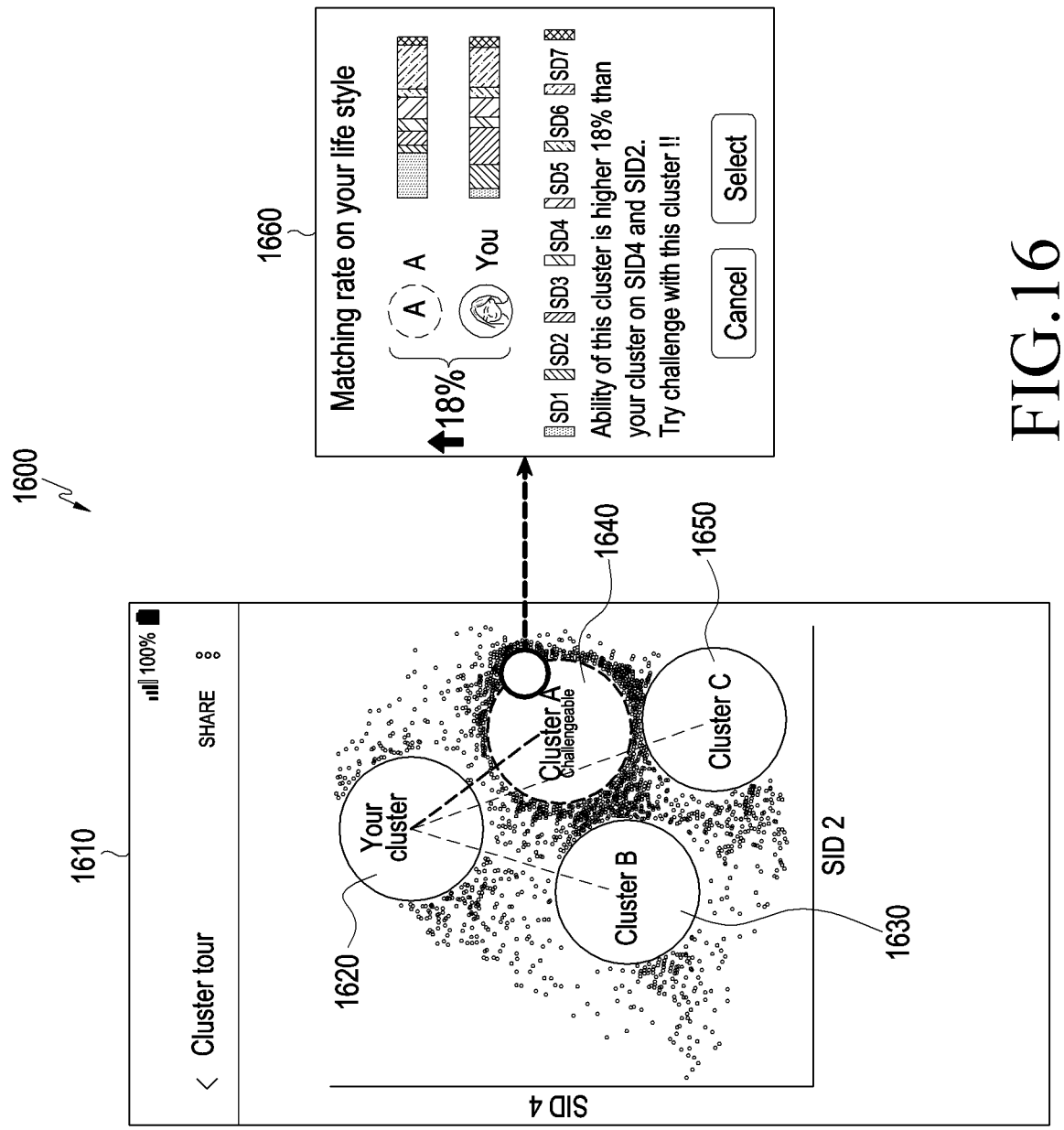
FIG. 16 is a view illustrating an example of a comparison between a cluster where a user does belong compared to a cluster where the user does not belong, according to an embodiment.

FIG. 16 is a view 1600 illustrating an example of a comparison between a cluster where a user belongs and a cluster where the user does not belong, according to an embodiment.

The user may view information not only about the cluster 1620 where the user belongs but also about other clusters 1630, 1640, and 1650 where the user does not belong through the cluster tour screen 1610. For example, when the user selects the item 1325 for cluster touring for moving between the group of FIG. 13A where the user belongs and the other groups, the cluster tour screen 1610 may be displayed. When the user selects the cluster 1640 where the user does not belong, the user may view the detailed screen 1660 for the cluster 1640. Thus, the user may browse the users of other clusters as well as the cluster where he or she belongs, thus encouraging the user's goal for improving healthcare and promoting competition.

Figure 17:
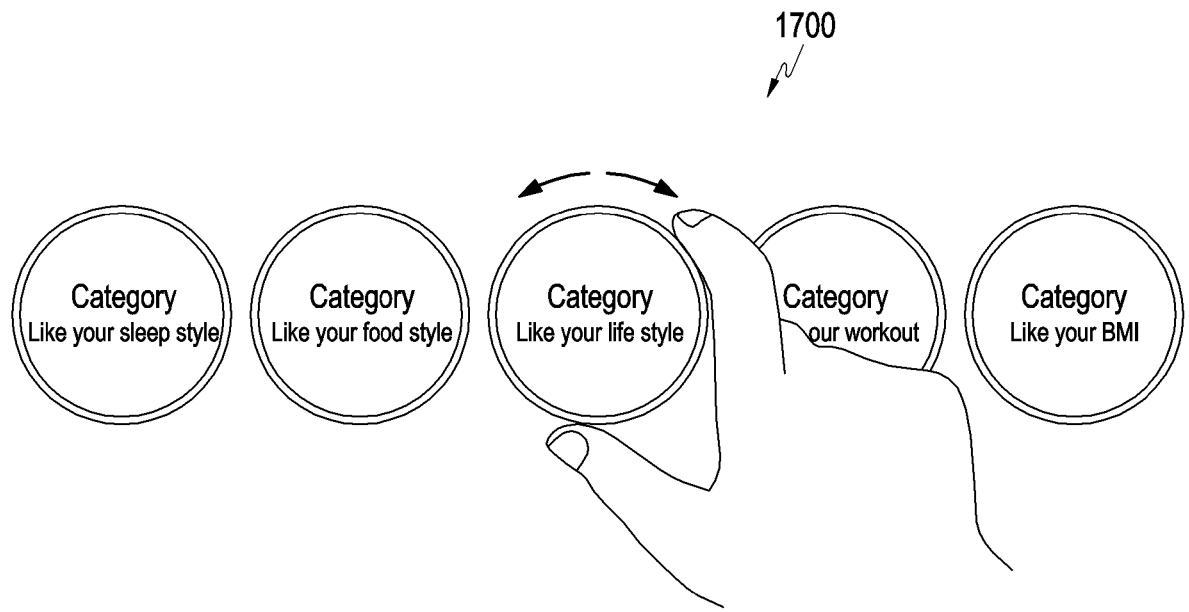
FIG. 17 is a view illustrating an example user interface outputting information for selecting a category on a wearable device, according to an embodiment.
Figure 18:
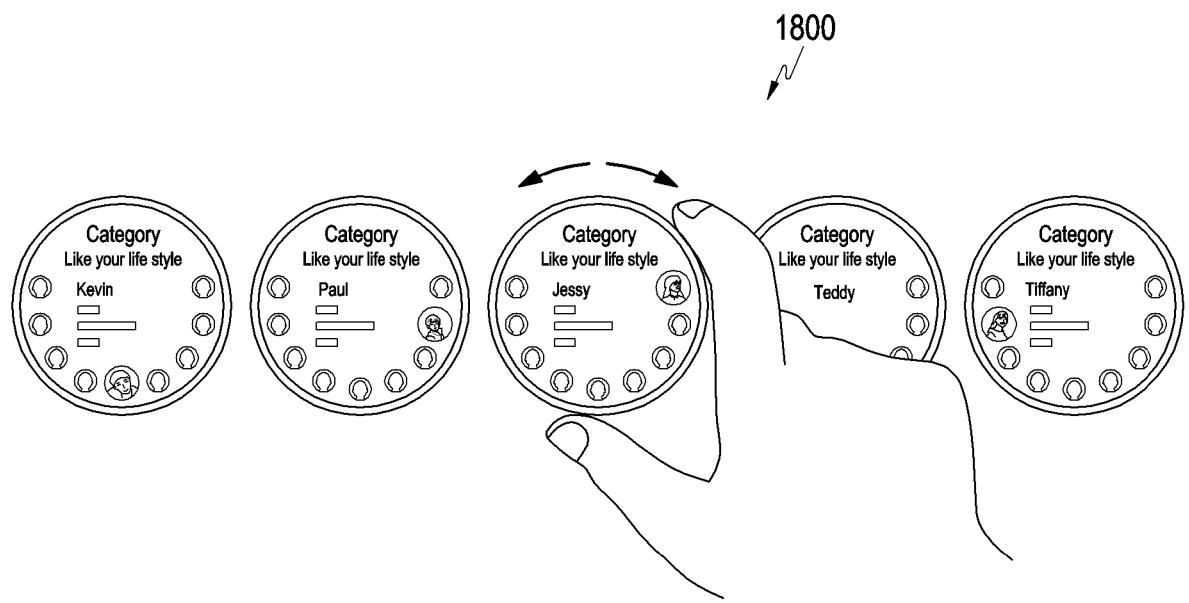
FIG. 18 is a view illustrating an example user interface outputting competitor information corresponding to a selected category on a wearable device, according to an embodiment.

FIG. 17 is a view 1700 illustrating an example user interface outputting information for category selection on a wearable device, according to an embodiment. FIG. 18 is a view 1800 illustrating an example user interface outputting competitor information corresponding to the selected category on a wearable device, according to an embodiment As shown in FIGS. 17 and 18, the user may browse categories and competitors in categories with the wheel of the wearable device or with screen touching.

Figure 19:
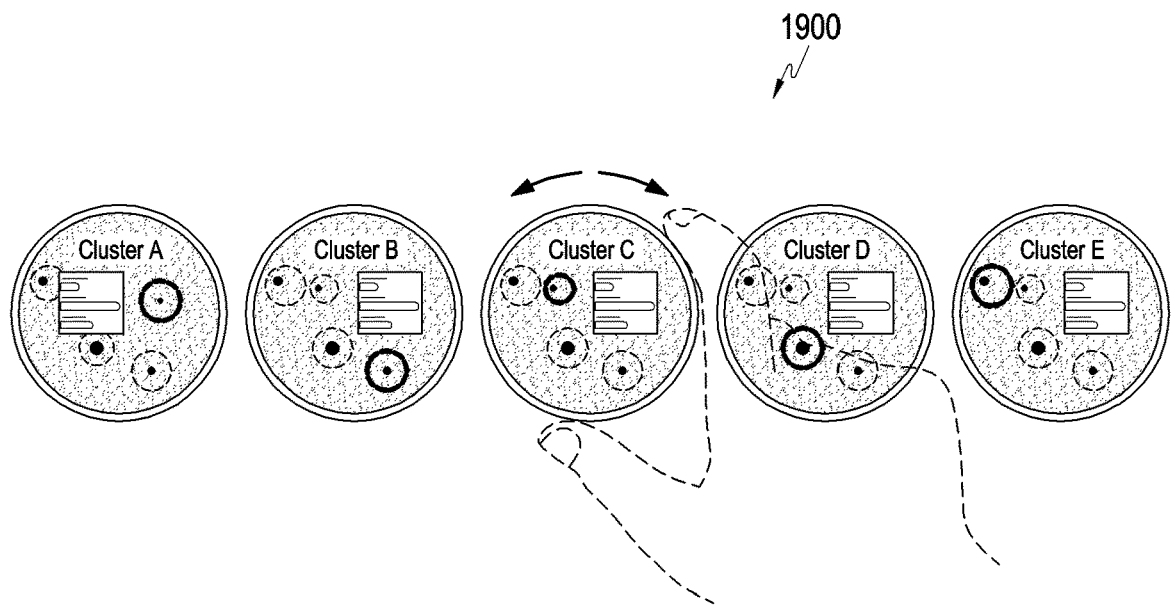
FIG. 19 is a view illustrating an example user interface outputting information about a cluster where a user belongs and a cluster where the user does not belong on a wearable device, according to an embodiment.

FIG. 19 is a view 1900 illustrating an example user interface outputting information about a cluster where a user belongs and a cluster where the user does not belong on a wearable device, according to an embodiment.

The user may view information not only about the cluster where the user belongs but also about other clusters where the user does not belong. FIG. 19 illustrates an example user interface which enables viewing of other clusters, e.g., clusters of other parties with different a propensity in the category the user selected on the watch-type wearable device. By providing such a cluster tour, the user may view information about other user groups as well as his or her own.

Figure 20:
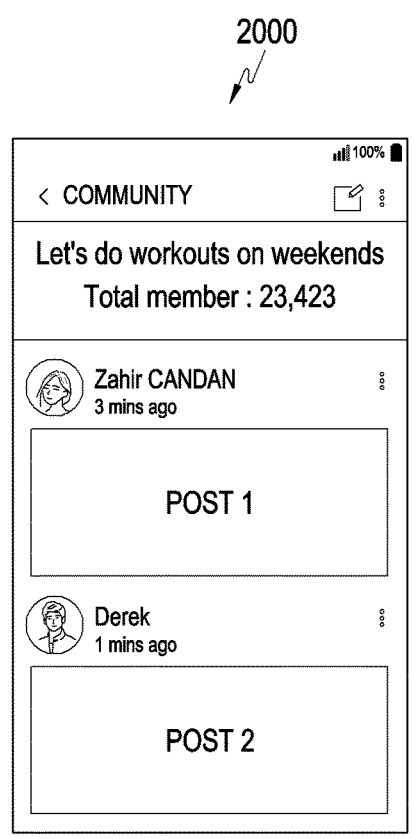
FIG. 20 is a view illustrating an example of using cluster information, according to an embodiment.

FIG. 20 is a view 2000 illustrating an example of using cluster information, according to an embodiment.

Various embodiments of the disclosure enable creation of a community as well as providing such a function as one-on-one competition or chatting for building a social network with competitors corresponding to the user's request. For example, when the user selects the item 1330 for identifying the community-related information of FIG. 13A, such a screen provides a function, e.g., creating a community, one-on-one competition or chatting for building a social network with competitors, which may be displayed. Since the community is formed based on the other parties who have a similar propensity to the user, the user may form an inter-user social network without performing a separate signup process.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Provided is a non-transitory storage medium storing instructions, the instructions configured to be executed by at least one processor to enable the at least one processor to perform at least one operation. The at least one operation comprises gathering data related to a first user, sending a request for a user group corresponding to a first category among a plurality of categories to an external server, obtaining the user group corresponding to the first category based on at least part of the first user-related data, and providing information about at least one second user in the obtained user group.

As is apparent from the foregoing description, the electronic device may gather all data which may have any effect on the user's healthcare and provide information about competitors who are most similar in activity pattern to the user.

The electronic device may quickly provide information about competitors who are most similar in activity pattern to the user corresponding to abrupt ambient variations, variations in activity or exercise record, or the user's various interests. This may encourage the user to maintain good healthcare habits and keep him or her using the healthcare service.

The electronic device may provide a user interface for displaying information about competitors which the user may compete with in a social relationship-type environment, thereby providing healthcare results and health information beneficial to the user that encourages the use to maintain good healthcare habits.

While the present disclosure has been particularly shown and described with reference to certain embodiments thereof, it will be understood by those of ordinary skill in the art that various changes in form and details may be made therein without departing from the spirit and scope of the disclosure as defined by the appended claims and their equivalents.

What is claimed is:

1. An electronic device, comprising:
   communication circuitry;
   a processor operatively connected with the communication circuitry; and
   a memory operatively connected with the processor, wherein the memory stores instructions configured to, when executed, enable the electronic device to:
   gather data related to a first user,
   send the data related to the first user to an external server using the communication circuitry,
   send a request for a user group corresponding to a first category among a plurality of categories to the external server using the communication circuitry,
   obtain the user group corresponding to the first category based on at least part of the data related to the first user from the external server using the communication circuitry, and
   provide information about at least one second user in the obtained user group, the at least one second user being at least one competitor with the first user,
   wherein the first user-related data includes a plurality of data types, and wherein the plurality of data types include at least one of personal information related to identification of the first user, competition information on a match between the first user and a competitor, activity information related to exercise of the first user, environment information related to weather, dietary information related to dietary habits of the first user, sleep information, service use information related to usage of an application, or use information of an external electronic device connected to the electronic device.

2. The electronic device of claim 1, wherein the memory is further configured to store an application based on the first user's activity, and wherein the instructions are further configured to enable the processor to display the information about the at least one second user on a display of the electronic device when the electronic device executes the application based on the first user's activity.

3. The electronic device of claim 1, wherein the instructions are further configured to enable the electronic device to:
   display an execution screen of an application based on the first user's activity, the execution screen including an item for selecting a first category, receive a selection of an item of a second category different from the first category, and obtain the second user group corresponding to the second category in response to the received selection, and display information about at least one third user in the obtained user group.

4. The electronic device of claim 3, wherein the first category is based on a first set of data types related to the first user and the second category is based on a second set of data types related to the first user.

5. The electronic device of claim 1, wherein the instructions are further configured to enable the electronic device to quantify the gathered first user-related data corresponding to each data type and provide the first user-related data quantified per data type to the external server using the communication circuitry.

6. The electronic device of claim 5, wherein the first user group corresponding to the first category is obtained based on at least part of data associated with the first category of the first user-related data quantified per data type.

7. The electronic device of claim 1, further comprising a sensor module operatively connected with the processor, wherein the instructions are further configured to enable the electronic device to gather the first user-related data using at least one sensor included in the sensor module.

8. The electronic device of claim 1, wherein the instructions are further configured to enable the electronic device to receive the first user-related data from an external electronic device using the communication circuitry and transmit the information about the at least one second user to the external electronic device using the communication circuitry.

9. An electronic device, comprising:
communication circuitry;
a processor; and
a memory operatively connected with the processor, wherein the memory stores instructions configured to, when executed, enable the electronic device to:
receive data related to a first user of an external electronic device from the external electronic device using the communication circuitry,
receive a request for a user group corresponding to a first category among a plurality of categories from the external electronic device using the communication circuitry,
obtain the user group corresponding to the first category based on at least part of the first user-related data, in response to the reception of the request, and
provide information about at least one second user in the obtained user group to the external electronic device using the communication circuitry,
wherein the first user-related data includes a plurality of data types, and wherein the plurality of data types include at least one of personal information related to identification of the first user, competition information on a match between the first user and a competitor, activity information related to exercise of the first user, environment information related to weather, dietary information related to dietary habits of the first user, sleep information, service use information related to usage of an application, or use information of an external electronic device connected to the electronic device.

10. The electronic device of claim 9; wherein the information about the at least one second user is displayed on a display of the external electronic device when the external electronic device executes an application based on the first user's activity.

11. The electronic device of claim 9, wherein the instructions are further configured to enable the electronic device to obtain user groups corresponding to each of the plurality of categories, respectively, based on the at least part of the first user-related data, in response to the reception of the request and provide the user groups corresponding to each of the plurality of categories to the external electronic device using the communication circuitry.

12. The electronic device of claim 9, wherein the instructions are further configured to enable the electronic device to:
identify the at least part of the first user-related data corresponding to the first category,
cluster the identified data by applying a feature extraction model to the identified data, and
identify the user group corresponding to the first category based on at least part of the clustered data.

13. The electronic device of claim 12, wherein the instructions are further configured to enable the electronic device to identify a user group closest to the first user based on the at least part of the clustered data.

14. The electronic device of claim 12, wherein the extraction model is a principal component analysis (PCA).

15. A method for providing a recommendation service on an electronic device, the method comprising:
gathering data related to a first user;
sending the data related to the first user to an external server;
sending a request for a user group corresponding to a first category among a plurality of categories to the external server;
obtaining the user group corresponding to the first category based on at least part of the first user-related data from the external server; and
providing information about at least one second user in the obtained user group,
wherein the first user-related data includes a plurality of data types, and
wherein the plurality of data types include at least one of personal information related to identification of the first user, competition information on a match between the first user and a competitor, activity information related to exercise of the first user, environment information related to weather, dietary information related to dietary habits of the first user, sleep information, service use information related to usage of an application, or use information of an external electronic device connected to the electronic device.

16. The method of claim 15, wherein providing the information about the at least one second user includes outputting the information on a display of the electronic device upon executing an application based on the first user's activity.

17. The method of claim 15, further comprising:
quantifying the gathered first user-related data corresponding to each data type; and
providing the first user-related data quantified per data type to the server.

18. The method of claim 17, wherein the user group corresponding to the first category is obtained based on at least part of data associated with the first category of the first user-related data quantified per data type.

19. A non-transitory storage medium storing instructions, the instructions configured to be executed by at least one processor of an electronic device to enable the electronic device to perform at least one operation, the at least one operation comprising:

gathering data related to a first user;

sending the data related to the first user to an external server;

sending a request for a user group corresponding to a first category among a plurality of categories to an external server;

obtaining the user group corresponding to the first category based on at least part of the first user-related data; and providing information about at least one second user in the obtained user group, wherein the first user-related data includes a plurality of data types, and wherein the plurality of data types include at least one of personal information related to identification of the first user, competition information on a match between the first user and a competitor, activity information related to exercise of the first user, environment information related to weather, dietary information related to dietary habits of the first user, sleep information, service use information related to usage of an application, or use information of an external electronic device connected to the electronic device.

* * * * *

UNITED STATES PATENT AND TRADEMARK OFFICE
CERTIFICATE OF CORRECTION

| | |
|---|---|
| PATENT NO. | : 11,600,382 B2 |
| APPLICATION NO. | : 16/654719 |
| DATED | : March 7, 2023 |
| INVENTOR(S) | : Kwansu Park |

It is certified that error appears in the above-identified patent and that said Letters Patent is hereby corrected as shown below:

In the Claims

In Column 29, Line 63 in Claim 10:
"10. The electronic device of claim 9; wherein the infor-"
Should be:
-- 10. The electronic device of claim 9, wherein the infor- --

In Column 30, Line 22 in Claim 14:
"14. The electronic device of claim 12, wherein the extrac-"
Should be:
-- 14. The electronic device of claim 12, wherein the feature extrac- --

Signed and Sealed this
Thirty-first Day of October, 2023

Katherine Kelly Vidal
*Director of the United States Patent and Trademark Office*